US011911089B2

(12) United States Patent
Worrell et al.

(10) Patent No.: US 11,911,089 B2
(45) Date of Patent: Feb. 27, 2024

(54) LEAD SCREW ASSEMBLY FOR ARTICULATION CONTROL IN SURGICAL INSTRUMENT

(71) Applicant: Ethicon LLC, Guaynabo, PR (US)

(72) Inventors: Barry C. Worrell, Centerville, OH (US); Geoffrey S. Strobl, Williamsburg, OH (US); Kipp M. Rupp, New Richmond, OH (US)

(73) Assignee: Cilag GmbH International, Zug (CH)

( * ) Notice: Subject to any disclaimer, the term of this patent is extended or adjusted under 35 U.S.C. 154(b) by 313 days.

(21) Appl. No.: 17/128,278

(22) Filed: Dec. 21, 2020

(65) Prior Publication Data

US 2021/0106378 A1    Apr. 15, 2021

Related U.S. Application Data

(63) Continuation of application No. 15/499,322, filed on Apr. 27, 2017, now Pat. No. 10,881,451.

(51) Int. Cl.
*A61B 18/14* (2006.01)
*A61B 17/29* (2006.01)
(Continued)

(52) U.S. Cl.
CPC ...... *A61B 18/1445* (2013.01); *A61B 17/2909* (2013.01); *A61B 2017/003* (2013.01);
(Continued)

(58) Field of Classification Search
CPC ...... A61B 2017/00327; A61B 18/1445; A61B 2018/00202; A61B 2017/003;
(Continued)

(56) References Cited

U.S. PATENT DOCUMENTS 4,351,332 A    9/1982 Whitney et al.
4,805,823 A    2/1989 Rothfuss
(Continued)

OTHER PUBLICATIONS

Shaft Collars, G.L. Huyett Key Stock Catalog, 2016, pp. 146-147, and Press Release announcing publication of new Key Stock catalog, Oct. 31, 2016, retrieved from https://www.huyett.com/AboutUs/News/Press-Release-2016-10-31, 8 pages.
(Continued)

*Primary Examiner* — Sean W Collins
(74) *Attorney, Agent, or Firm* — Frost Brown Todd LLP

(57) ABSTRACT

An apparatus includes a body, a shaft assembly, an articulation section, an end effector, an articulation connector, and an articulation drive assembly. The shaft assembly extends distally from the body. The end effector is connected to the articulation section such that the end effector is configured to deflect relative to the longitudinal axis of the shaft assembly. The articulation connector is configured to translate relative to the shaft assembly to deflect the end effector relative to the longitudinal axis. The articulation drive assembly is configured to translate the articulation connector relative to the shaft assembly. The articulation drive assembly includes a rotatable housing and a first lead screw assembly. The first lead screw assembly includes a first half and a second half. The first lead screw assembly is slidably coupled with the shaft assembly and is configured to translate in response to rotation of the rotatable housing.

19 Claims, 35 Drawing Sheets

(51) Int. Cl.
*A61B 18/00* (2006.01)
*A61B 17/00* (2006.01)

(52) U.S. Cl.
CPC ............... *A61B 2017/00327* (2013.01); *A61B 2017/294* (2013.01); *A61B 2017/2925* (2013.01); *A61B 2017/2936* (2013.01); *A61B 2018/00202* (2013.01); *A61B 2018/1455* (2013.01)

(58) Field of Classification Search
CPC ........ A61B 17/2909; A61B 2018/1455; A61B 2017/294; A61B 2017/2936; A61B 2017/2925; F16H 25/06; F16H 25/12; F16H 25/122
See application file for complete search history.

(56) References Cited

U.S. PATENT DOCUMENTS

| | | | |
|---|---|---|---|
| 5,152,779 A | 10/1992 | Sanagi | |
| 5,237,886 A | 8/1993 | Kellar | |
| 5,415,334 A | 5/1995 | Williamson et al. | |
| 5,465,895 A | 11/1995 | Knodel et al. | |
| 5,490,819 A | 2/1996 | Nicholas et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,500,176 B1 | 12/2002 | Truckai et al. | |
| 6,783,524 B2 | 8/2004 | Anderson et al. | |
| 6,799,930 B1 * | 10/2004 | More | F16B 37/0892 411/278 |
| 6,978,921 B2 | 12/2005 | Shelton et al. | |
| 7,000,818 B2 | 2/2006 | Shelton et al. | |
| 7,112,201 B2 | 9/2006 | Truckai et al. | |
| 7,125,409 B2 | 10/2006 | Truckai et al. | |
| 7,143,923 B2 | 12/2006 | Shelton et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,303,108 B2 | 12/2007 | Shelton et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,381,209 B2 | 6/2008 | Truckai et al. | |
| 7,404,508 B2 | 7/2008 | Smith et al. | |
| 7,434,715 B2 | 10/2008 | Shelton et al. | |
| 7,721,930 B2 | 5/2010 | McKenna et al. | |
| 8,408,439 B2 | 4/2013 | Huang et al. | |
| 8,453,914 B2 | 6/2013 | Laurent et al. | |
| 8,461,744 B2 | 6/2013 | Wiener et al. | |
| 8,888,809 B2 | 11/2014 | Davison et al. | |
| 8,939,974 B2 | 1/2015 | Boudreaux et al. | |
| 8,986,302 B2 | 3/2015 | Aldridge et al. | |
| 9,089,327 B2 | 7/2015 | Worrell et al. | |
| 9,161,803 B2 | 10/2015 | Yates et al. | |
| 9,402,682 B2 | 8/2016 | Worrell et al. | |
| 9,492,224 B2 | 11/2016 | Boudreaux et al. | |
| 9,526,565 B2 | 12/2016 | Strobl | |
| 9,545,253 B2 | 1/2017 | Worrell et al. | |
| 10,881,451 B2 * | 1/2021 | Worrell | A61B 18/1445 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2012/0078243 A1 * | 3/2012 | Worrell | A61B 17/07207 606/130 |
| 2013/0023868 A1 * | 1/2013 | Worrell | A61B 17/07207 606/205 |
| 2014/0005681 A1 | 1/2014 | Gee et al. | |
| 2014/0276719 A1 | 9/2014 | Parihar | |
| 2015/0320437 A1 | 11/2015 | Worrell et al. | |
| 2016/0100882 A1 | 4/2016 | Boudreaux et al. | |
| 2016/0302820 A1 | 10/2016 | Hibner et al. | |

OTHER PUBLICATIONS

Extended European Search Report and Written Opinion dated Jan. 13, 2021, for Application No. 18791832.1, 5 pages.
International Search Report and Written Opinion dated Jul. 5, 2018, for International Application No. PCT/US2018/027770, 15 pages.
U.S. Appl. No. 61/410,603, entitled "Energy-Based Surgical Instruments," filed Nov. 5, 2010.
Chinese Office Action and Search Report dated Jul. 27, 2022, for Application No. CN 201880031135.0, 15 pages.
Japanese Notification of Reasons for Refusal dated Mar. 29, 2022, for Application No. JP 2019-558610, 5 pages.

* cited by examiner

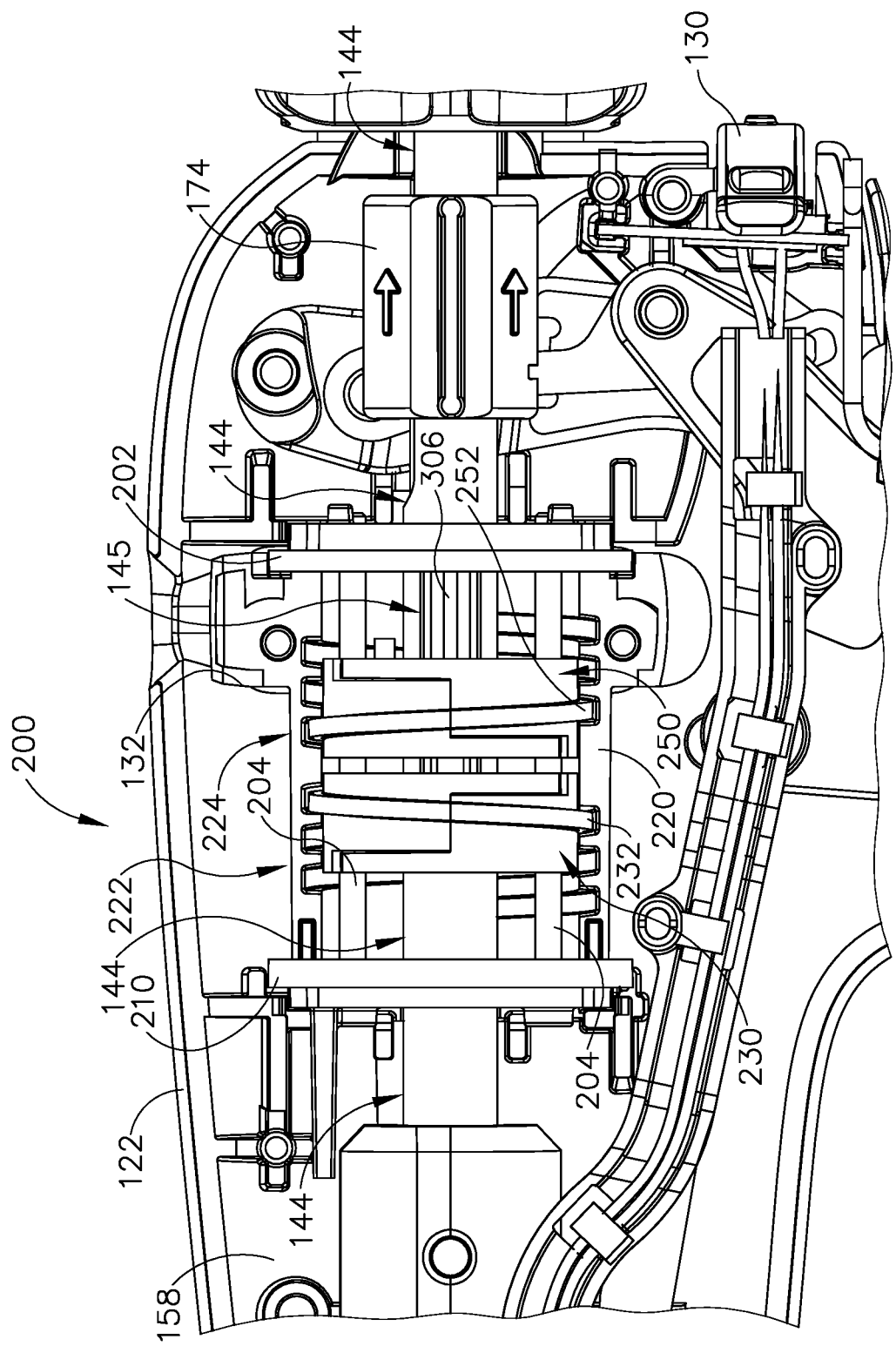

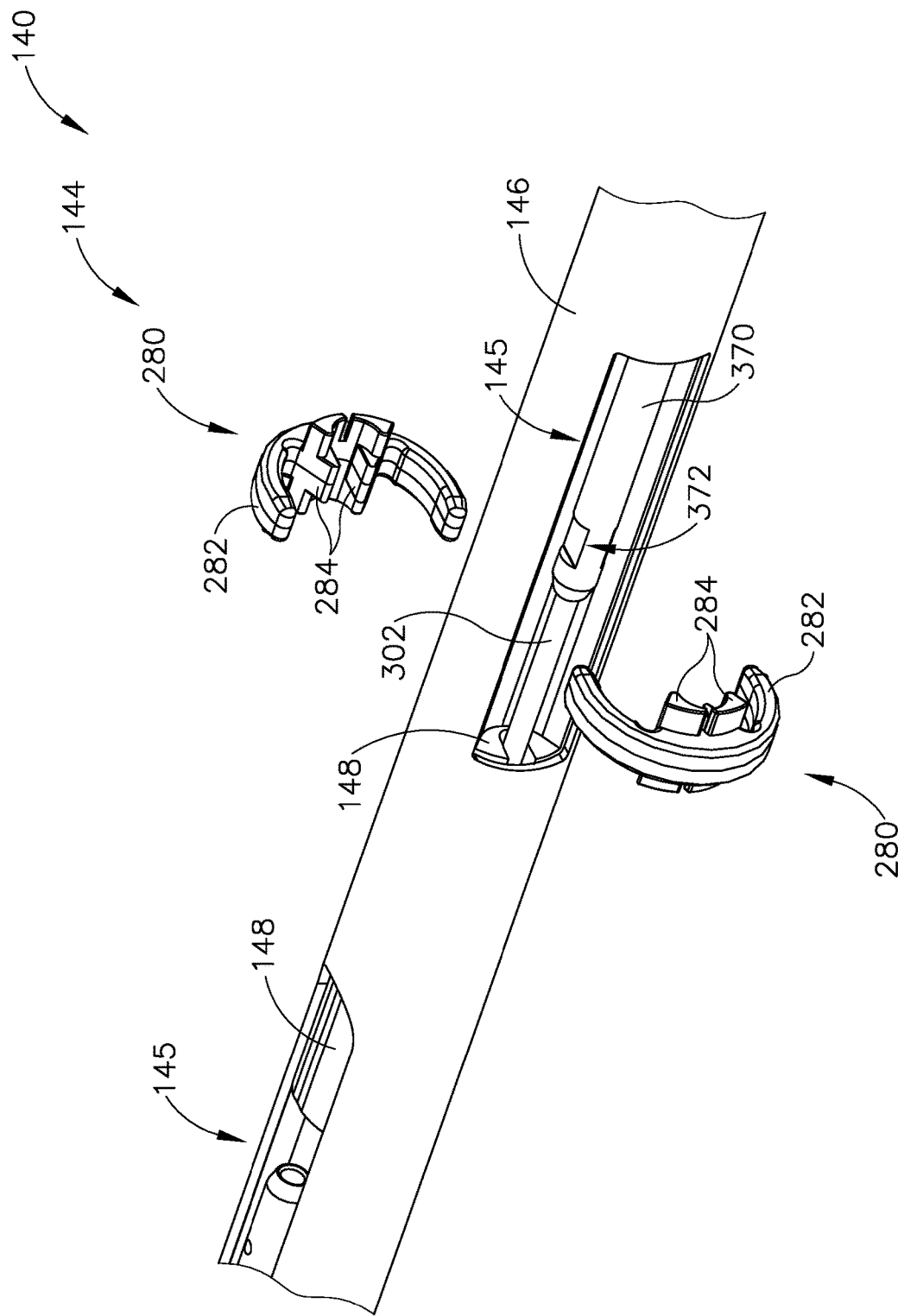

LEAD SCREW ASSEMBLY FOR ARTICULATION CONTROL IN SURGICAL INSTRUMENT

This application is a continuation of U.S. patent application Ser. No. 15/499,322, entitled "Lead Screw Assembly for Articulation Control in Surgical Instrument," filed Apr. 27, 2017 and issued as U.S. Pat. No. 10,881,451 on Jan. 5, 2021.

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0083783, entitled "Surgical Instrument with Jaw Member," published Apr. 5, 2012, issued as U.S. Pat. No. 8,888,809 on Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pub. No. 2012/0078247, entitled "Articulation Joint Features for Articulating Surgical Device," published Mar. 29, 2012, issued as U.S. Pat. No. 9,402,682 on Aug. 2, 2016 the disclosure of which is incorporated by reference herein; U.S. Pub. No. 2013/0030428, entitled "Surgical Instrument with Multi-Phase Trigger Bias," published Jan. 31, 2013, issued as U.S. Pat. No. 9,089,327 on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, issued as U.S. Pat. No. 9,545,253 on Jan. 17, 2017, the disclosure of which is incorporated by reference herein.

Still other examples of electrosurgical cutting instruments and related concepts are disclosed in U.S. Pat. No. 9,526,565, entitled "Electrosurgical Devices," issued Dec. 27, 2016, the disclosure of which is incorporated by reference herein; U.S. Pat. No. 9,492,224, entitled "Multi-Function Bi-Polar Forceps," issued Nov. 15, 2016, the disclosure of which is incorporated by reference herein; and U.S. Pub. No. 2016/0100882, entitled "Methods and Devices for Articulating Laparoscopic Energy Device," published Apr. 14, 2016, issued as U.S. Pat. No. 10,292,758 on May 21, 2019, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9C depicts an elevational side view of the handle assembly of FIG. 7A, where the articulation assembly of FIG. 2 is in a second articulated configuration, were selected portions of the handle assembly are omitted for purposes of clarity;

FIG. 23A depicts a perspective view of a pair of exemplary coupling members of the lead screw assembly of FIG. 15 aligned to be attached to respective articulation connectors;

Figure 1:
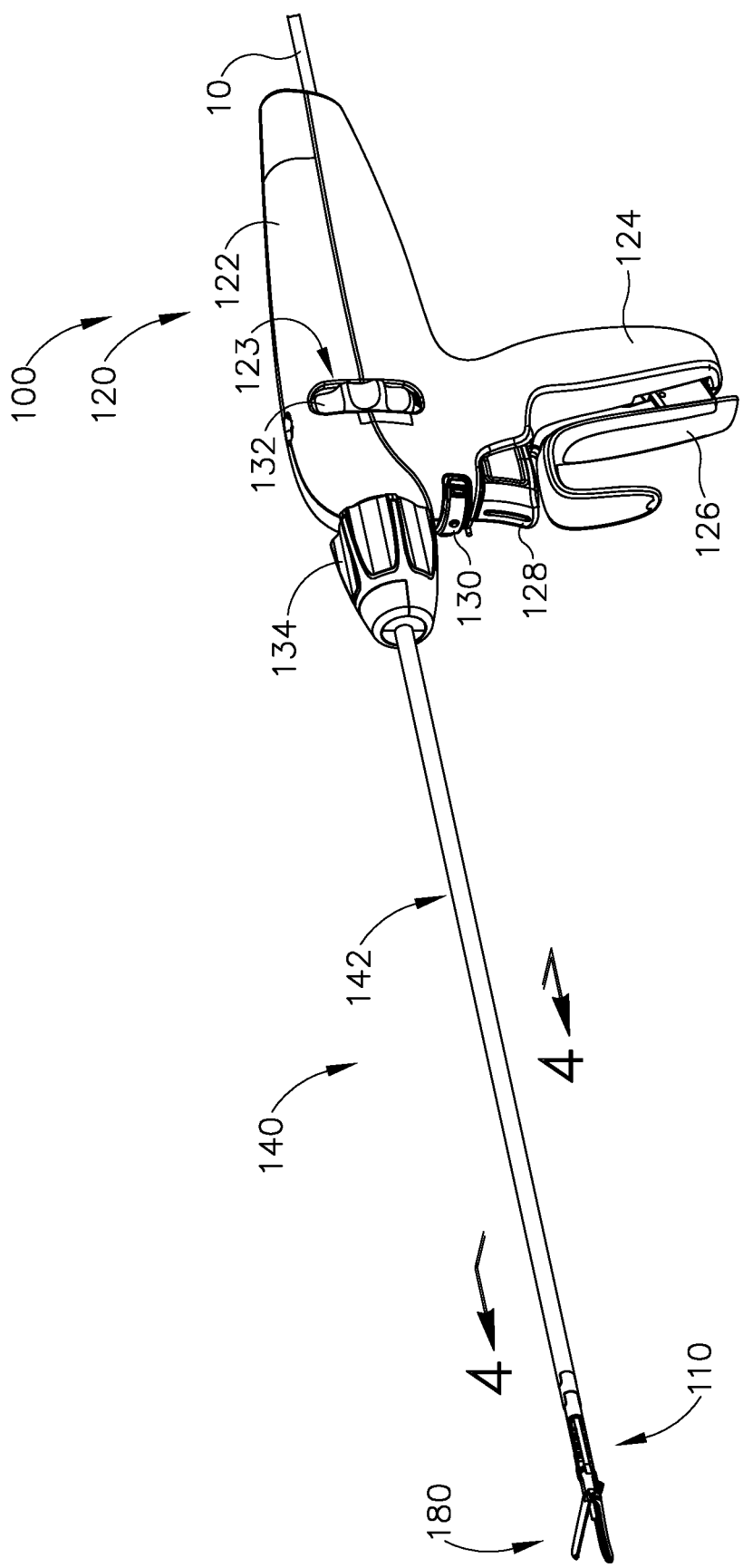
FIG. 1 depicts a perspective view of an exemplary electrosurgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. EXEMPLARY ELECTROSURGICAL INSTRUMENT

FIGS. 1-10 show an exemplary electrosurgical instrument (100). As best seen in FIG. 1, electrosurgical instrument (100) includes a handle assembly (120), a shaft assembly (140), an articulation assembly (110), and an end effector (180). As will be described in greater detail below, end effector (180) of electrosurgical instrument (100) is operable to grasp, cut, and seal or weld tissue (e.g., a blood vessel, etc.). In this example, end effector (180) is configured to seal or weld tissue by applying bipolar radio frequency (RF) energy to tissue. However, it should be understood electrosurgical instrument (100) may be configured to seal or weld tissue through any other suitable means that would be apparent to one having ordinary skill in the art in view of the teachings herein. For example, electrosurgical instrument (100) may be configured to seal or weld tissue via an ultrasonic blade, staples, etc. In the present example, electrosurgical instrument (100) is electrically coupled to a power source (not shown) via power cable (10).

The power source may be configured to provide all or some of the electrical power requirements for use of electrosurgical instrument (100). Any suitable power source may be used as would be apparent to one having ordinary skill in the art in view of the teachings herein. By way of example only, the power source may comprise a GEN04 or GEN11 sold by Ethicon Endo-Surgery, Inc. of Cincinnati, Ohio. In addition, or in the alternative, the power source may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. While in the current example, electrosurgical instrument (100) is coupled to a power spruce via power cable (10), electrosurgical instrument (100) may contain an internal power source or plurality of power sources, such as a battery and/or supercapacitors, to electrically power electrosurgical instrument (100). Of course, any suitable combination of power sources may be utilized to power electrosurgical instrument (100) as would be apparent to one having ordinary skill in the art in view of the teaching herein Handle assembly (120) is configured to be grasped by an operator with one hand, such that an operator may control and manipulate electrosurgical instrument (100) with a single hand. Shaft assembly (140) extends distally from handle assembly (120) and connects to articulation assembly (110). Articulation assembly (110) is also connected to a proximal end of end effector (180). As will be described in greater detail below, components of handle assembly (120) are configured to control end effector (180) such that an operator may grasp, cut, and seal or weld tissue. As will also be described in greater detail below, articulation assembly (110) is configured to deflect end effector (180) from the longitudinal axis defined by shaft assembly (140).

Handle assembly (120) includes a body (122), a pistol grip (124), a jaw closure trigger (126), a knife trigger (128), an activation button (130), an articulation control (132), and a knob (134). As will be described in greater detail below, jaw closure trigger (126) may be pivoted toward and away from pistol grip (124) and/or body (122) to open and close jaws (182, 184) of end effector (180) to grasp tissue. Knife trigger (128) may be pivoted toward and away from pistol grip (124) and/or body (122) to actuate a knife member (360) within the confines of jaws (182, 184) to cut tissue captured between jaws (182, 184). Activation button (130) may be pressed to apply radio frequency (RF) energy to tissue via electrode surfaces (194, 196) of jaws (182, 184), respectively.

Body (122) of handle assembly (120) defines an opening (123) in which a portion of articulation control (132) protrudes from. Articulation control (132) is rotatably disposed within body (122) such that an operator may rotate the portion of articulation control (132) protruding from opening (123) to rotate the portion of articulation control (132) located within body (122). As will be described in greater detail below, rotation of articulation control (132) relative to body (122) will drive deflection of end effector (180) from the longitudinal axis defined by shaft assembly (140).

Knob (134) is rotatably disposed on the distal end of body (122) and configured to rotate end effector (180), articulation assembly (110), and shaft assembly (140) about the longitudinal axis of shaft assembly (140) relative to handle assembly (120). While in the current example, end effector (180), articulation assembly (110), and shaft assembly (140) are rotated by knob (134), knob (134) may be configured to rotate end effector (180) and articulation assembly (110) relative to selected portions of shaft assembly (140). Knob (134) may include any suitable features to rotate end effector (180), articulation assembly (110), and shaft assembly (140) as would be apparent to one having ordinary skill in the art in view of the teachings herein.

Figure 4:
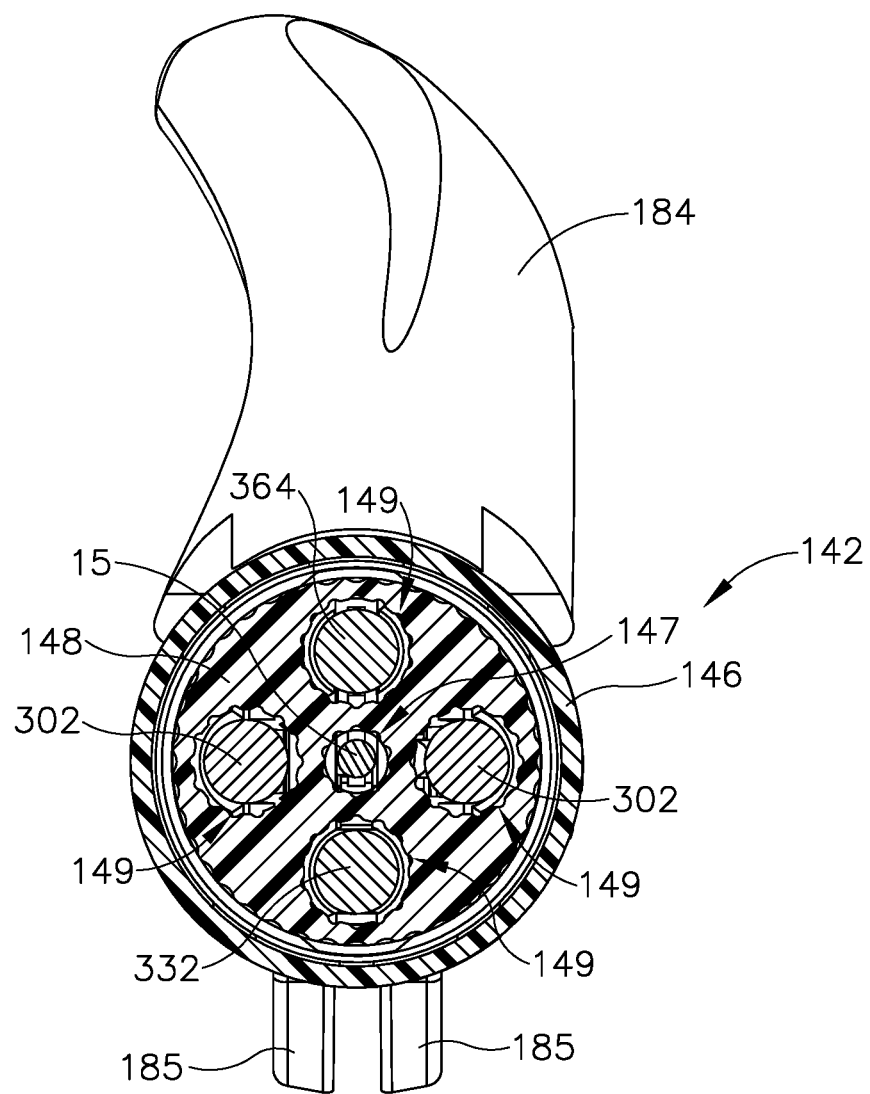
FIG. 4 depicts a cross-sectional rear view of a shaft assembly of the electrosurgical instrument of FIG. 1, taken along line 4-4 of FIG. 1.
Figure 7A:
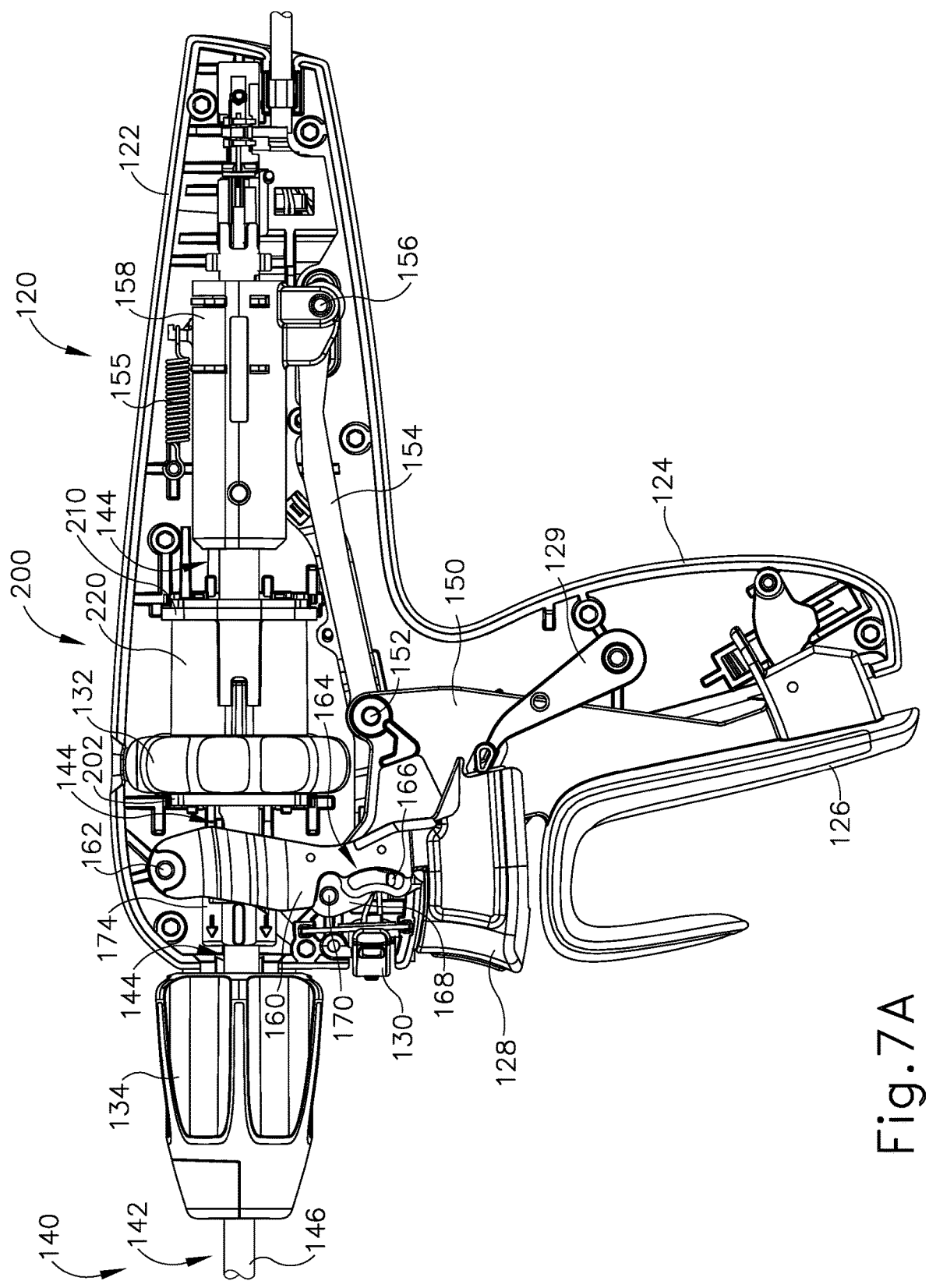
FIG. 7A depicts a side elevational view of a handle assembly of the electrosurgical instrument of FIG. 1, where the end effector is in an open and unfired state, where a portion of the handle assembly is omitted for purposes of clarity.
Figure 7B:
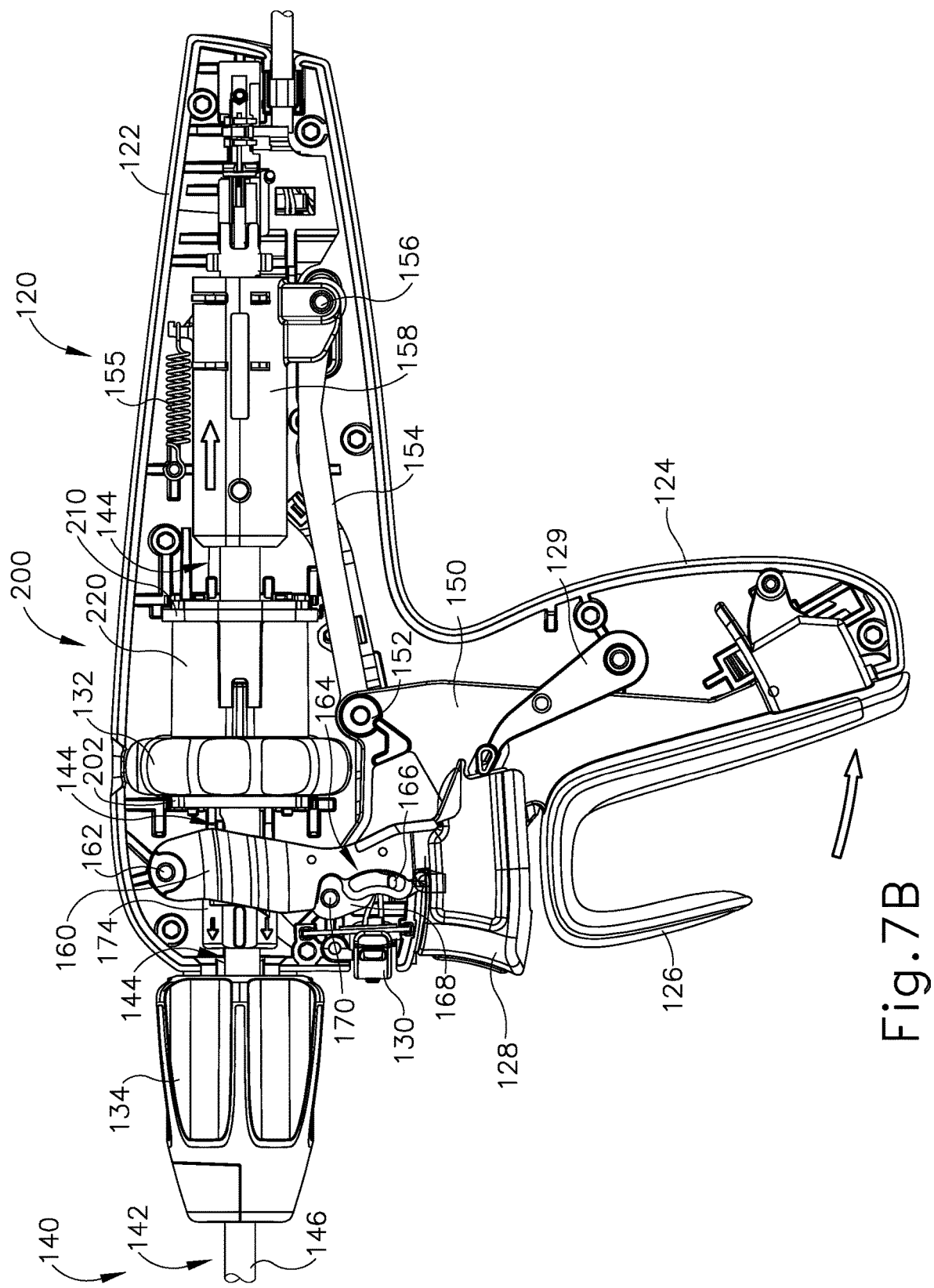
FIG. 7B depicts a side elevational view of the handle assembly of FIG. 7A, where the end effector is in a closed and unfired state, where a portion of the handle assembly is omitted for purposes of clarity.
Figure 7C:
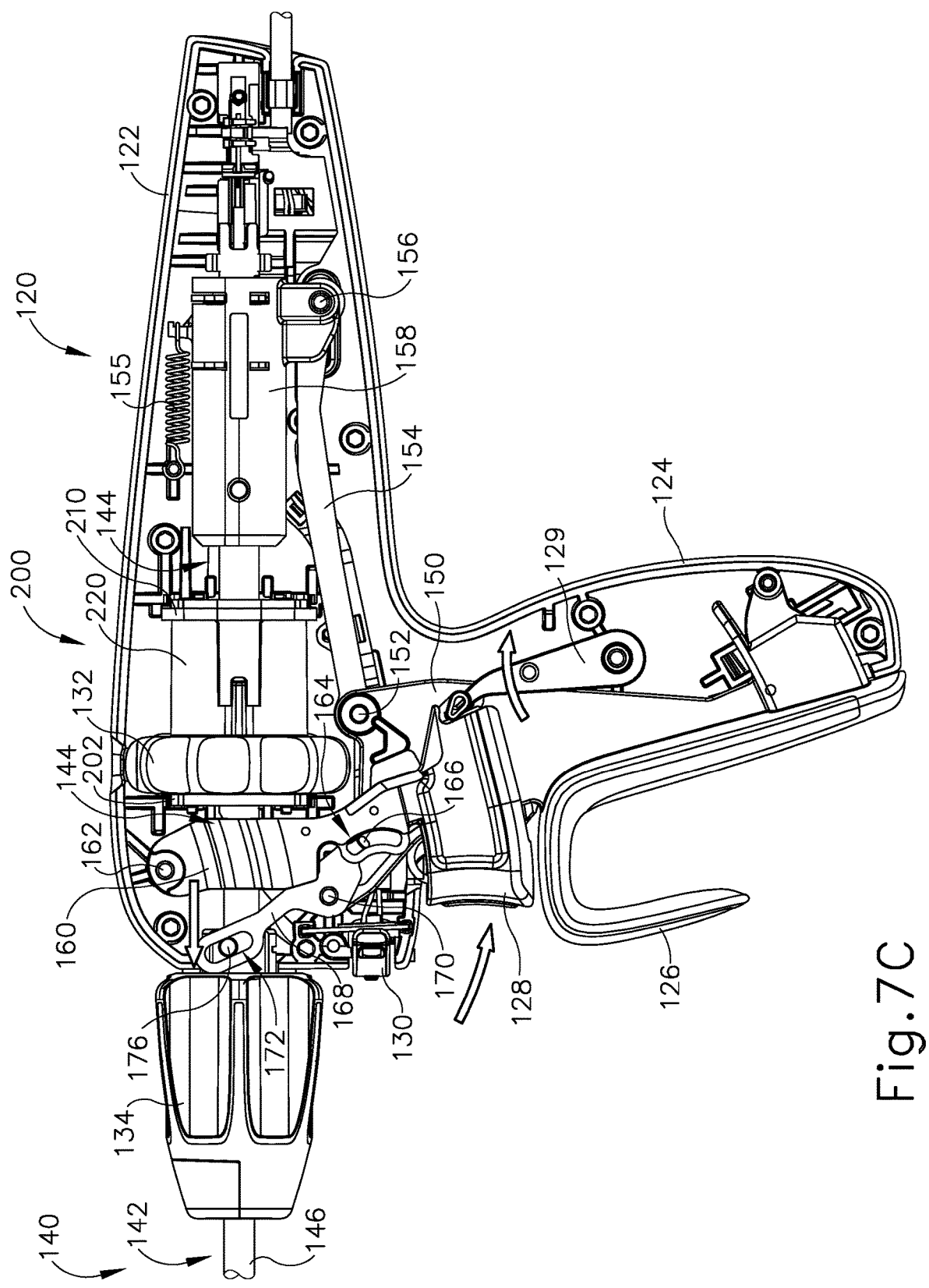
FIG. 7C depicts a side elevational view of the handle assembly of FIG. 7A, where the end effector is in a closed and fired state, where a portion of the handle assembly is omitted for purposes of clarity.

As best seen in FIGS. 7A-7C, shaft assembly (140) includes distal portion (142) extending distally from handle assembly (120), and a proximal portion (144) housed within the confines of body (122) of handle assembly (120). As seen in FIG. 4, distal portion (142) of shaft assembly (140) includes an external sheath (146) and a housing member (148) disposed within external sheath (146). Housing member (148) defines four longitudinal pathways (149) disposed around a central longitudinal pathway (147). Longitudinal pathways (149) slidably house two rod portions (302) of two articulation connectors (300), a rod portion (332) of jaw closure connector (330), and a knife rod (364) of knife member (360); while central longitudinal pathway (147) houses electrical coupling (15). As will be described in greater detail below, articulation connectors (300) are configured to couple certain actuating portions of handle assembly (120) with end effector (180). Articulation connectors (300) are configured to translate relative to shaft assembly (140) to drive articulation of end effector (180) relative to the longitudinal axis defined by shaft assembly (140). As will also be described in greater detail below, jaw closure connector (330) is configured to couple an actuating portion of handle assembly (120) with end effector (180). Jaw closure connector (330) is configured to translate relative to shaft assembly (140) to open and close jaws (182, 184) of end effector (180). As will also be described in greater detail below, knife member (360) is configured to couple to an actuating portion of handle assembly (120) to translate a distal cutting edge (362) within the confines of end effector (180).

Figure 9A:
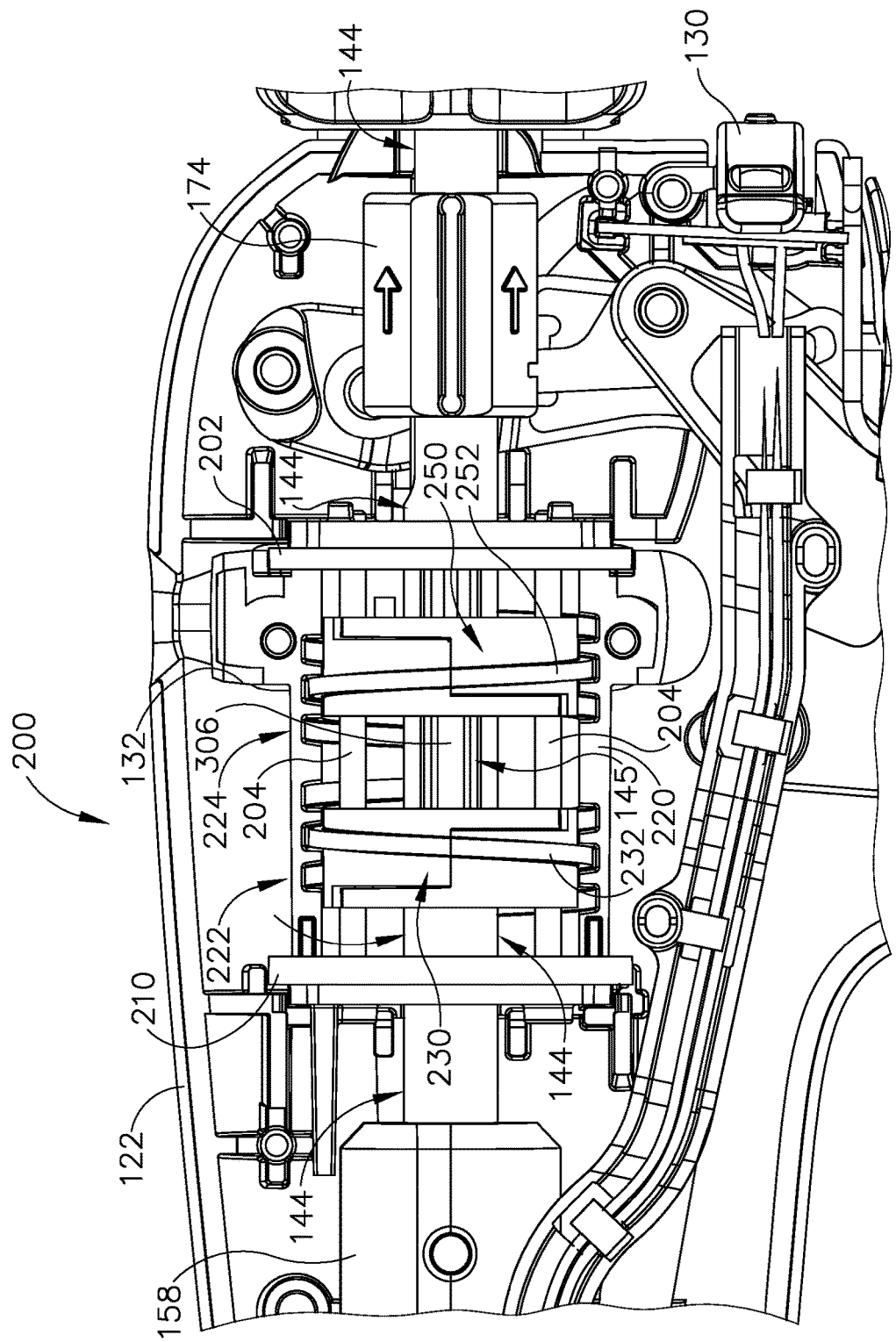
FIG. 9A depicts an elevational side view of the handle assembly of FIG. 7A, where the articulation assembly of FIG. 2 is a non-articulated configuration, where selected portions of the handle assembly are omitted for purposes of clarity.
Figure 9B:
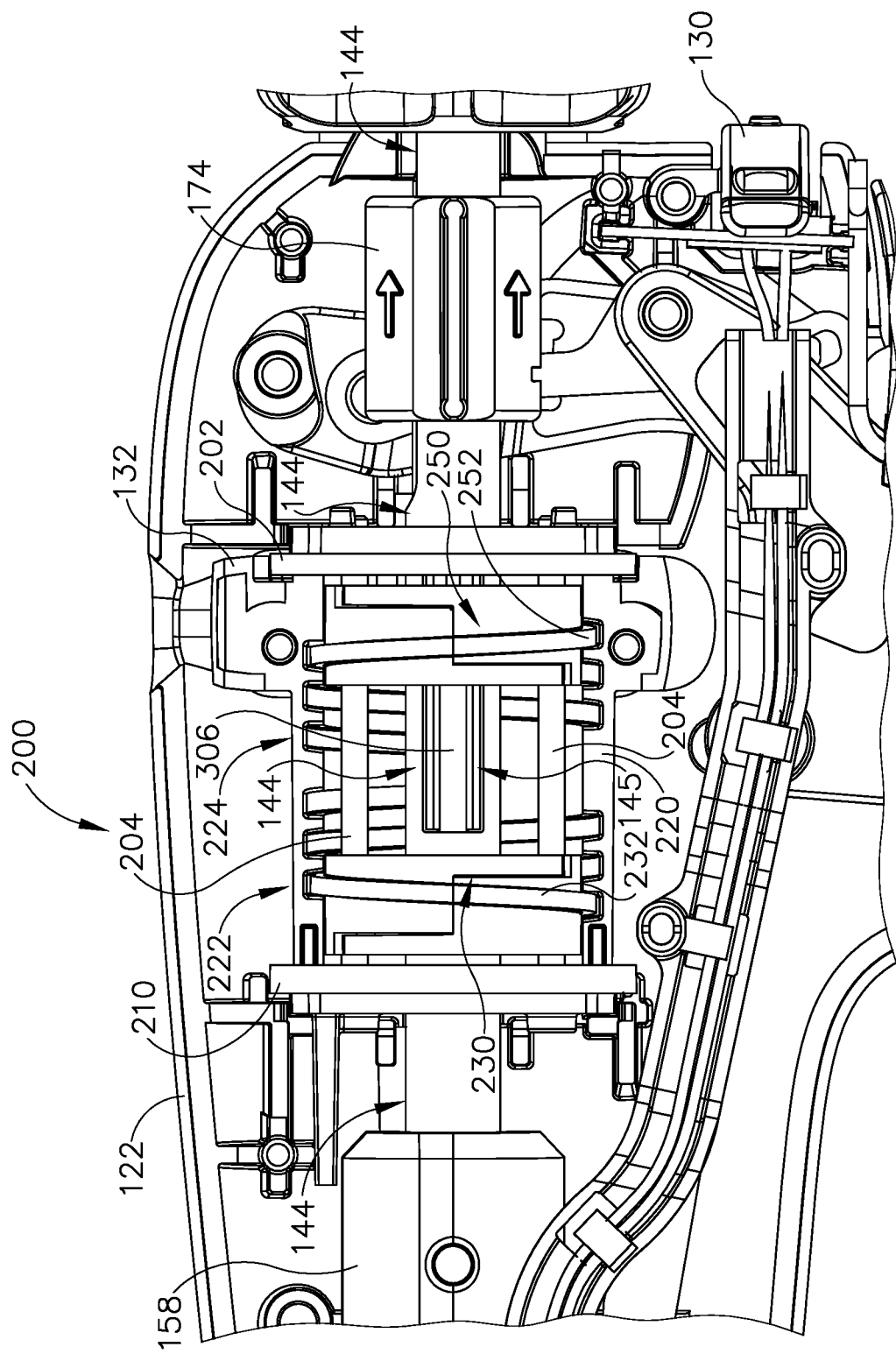
FIG. 9B depicts an elevational side view of the handle assembly of FIG. 7A, where the articulation assembly of FIG. 2 is in a first articulated configuration, were selected portions of the handle assembly are omitted for purposes of clarity.

As will be described in greater detail below, proximal portion (144) of shaft assembly (140) extends within handle assembly (120) and through certain actuating portions of handle assembly (120) that are configured to longitudinally drive rod portions (302, 332, 364). As will also be described in greater detail below, rod portions (302, 332, 364) extend within proximal portion (144) and couple with correspond actuating portions of handle assembly (120). As best shown in FIGS. 9A-9C, proximal portion (144) defines slots (145) to allow actuating portions of handle assembly (120) to couple with rod portions (302, 332, 364) such that translation of actuation portions of handle assembly (120) relative to shaft assembly (140) longitudinally drives rod portions (302, 332, 364) relative to shaft assembly (140). Rod portions (302, 332, 364) are coupled to certain actuating portions of handle assembly (120) such that rod portions (302, 332, 364) may rotate with shaft assembly (140) relative to actuating portions of handle assembly (120); but also such that rod portions (302, 332, 364) longitudinally translate with actuating portions of handle assembly (120) relative to shaft assembly (140). In other words, an operator may utilize knob (134) to rotate shaft assembly (140) and rod portions (302, 332, 364) relative to handle assembly (120); but also may actuate rod portions (302, 332, 364) longitudinally relative to shaft assembly (140).

Figure 2:
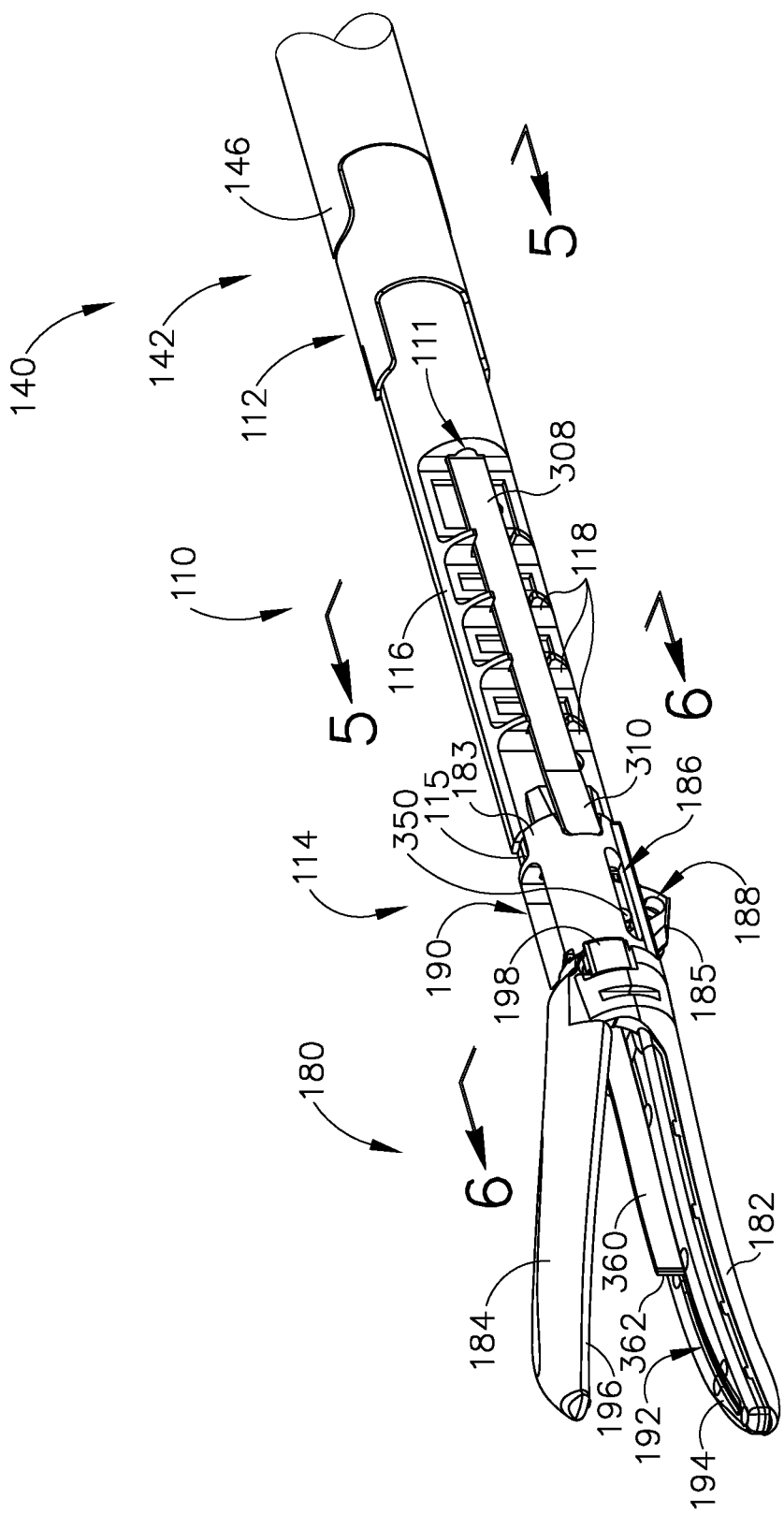
FIG. 2 depicts a perspective view of an exemplary articulation assembly and end effector of the electrosurgical instrument of FIG. 1.
Figure 3:
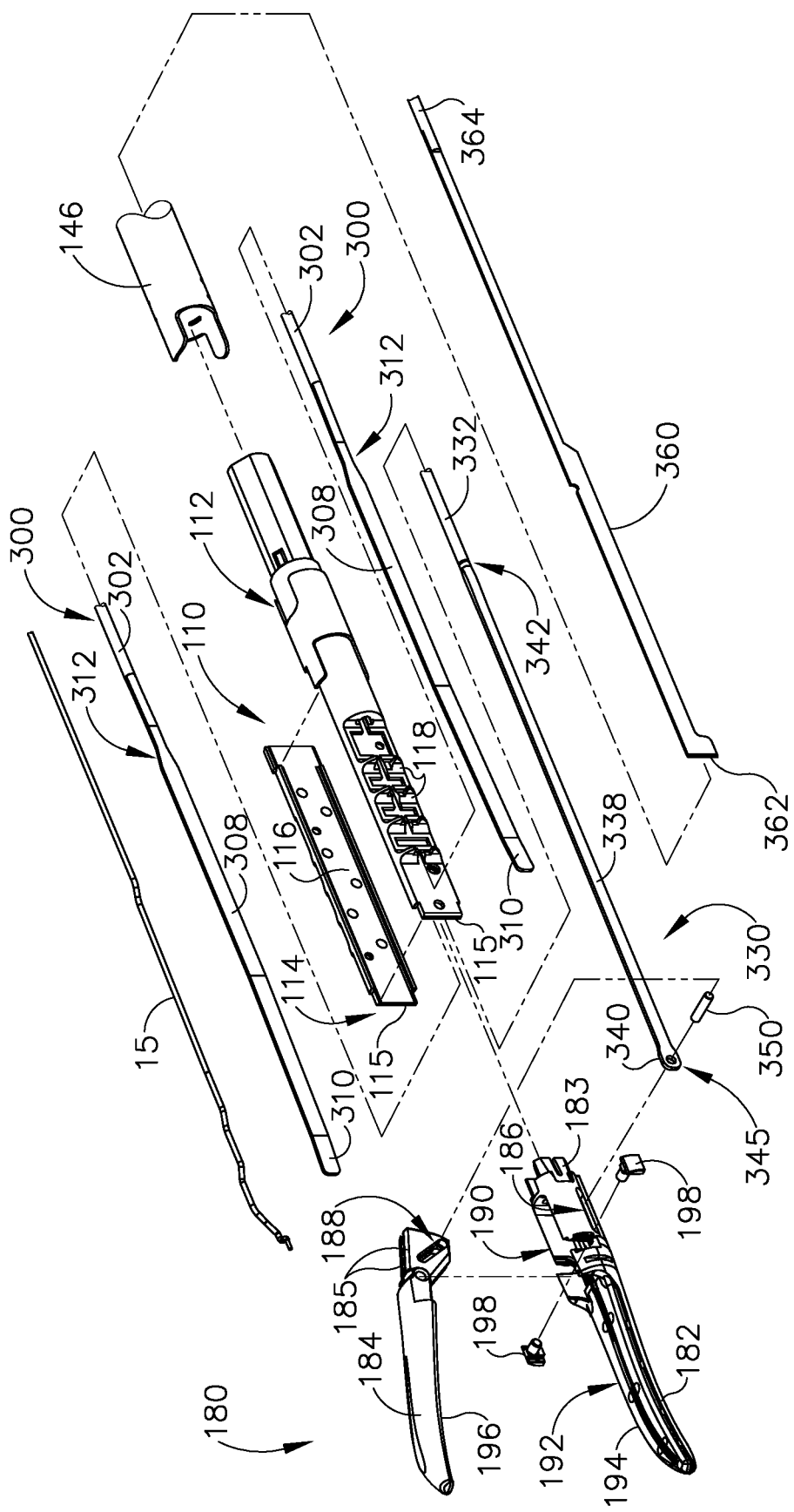
FIG. 3 depicts an exploded view of the articulation assembly and end effector of FIG. 2.
Figure 6:
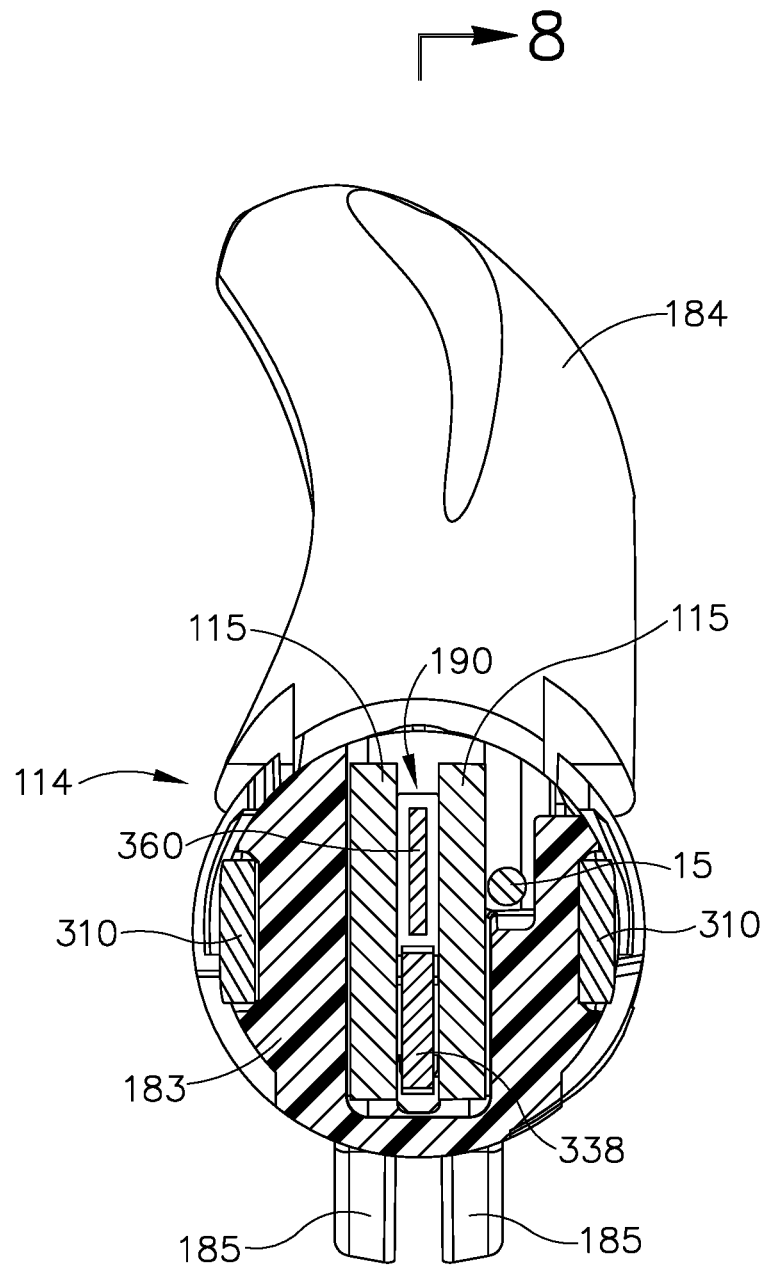
FIG. 6 depicts a cross-sectional rear view of the end effector of FIG. 2, taken along line 6-6 of FIG. 2.

FIGS. 2-3 show end effector (180), articulation assembly (110), and a distal portion (142) of shaft assembly (140). Articulation section (110) extends from a rigid proximal portion (112) to a distal portion (114). Rigid proximal portion (112) is fixed to outer sheath (146) of distal portion (142) of shaft assembly (140). As best seen in FIG. 6, distal portion (114) of articulation section (110) includes distal projections (115) inserted within the confines of proximal body (183) of lower jaw (182). A flexible member (116) extends from the distal end of rigid proximal portion (112) toward distal portion (114). As seen in FIG. 3, in the present example, two flexible members (116) are laterally coupled with each other such that both flexible members (116) extend along the same longitudinal axis. However, any other suitable combination or assembly of flexible members (116) may be used as would be apparent to one having ordinary skill in the art in view of the teachings herein.

Figure 10A:
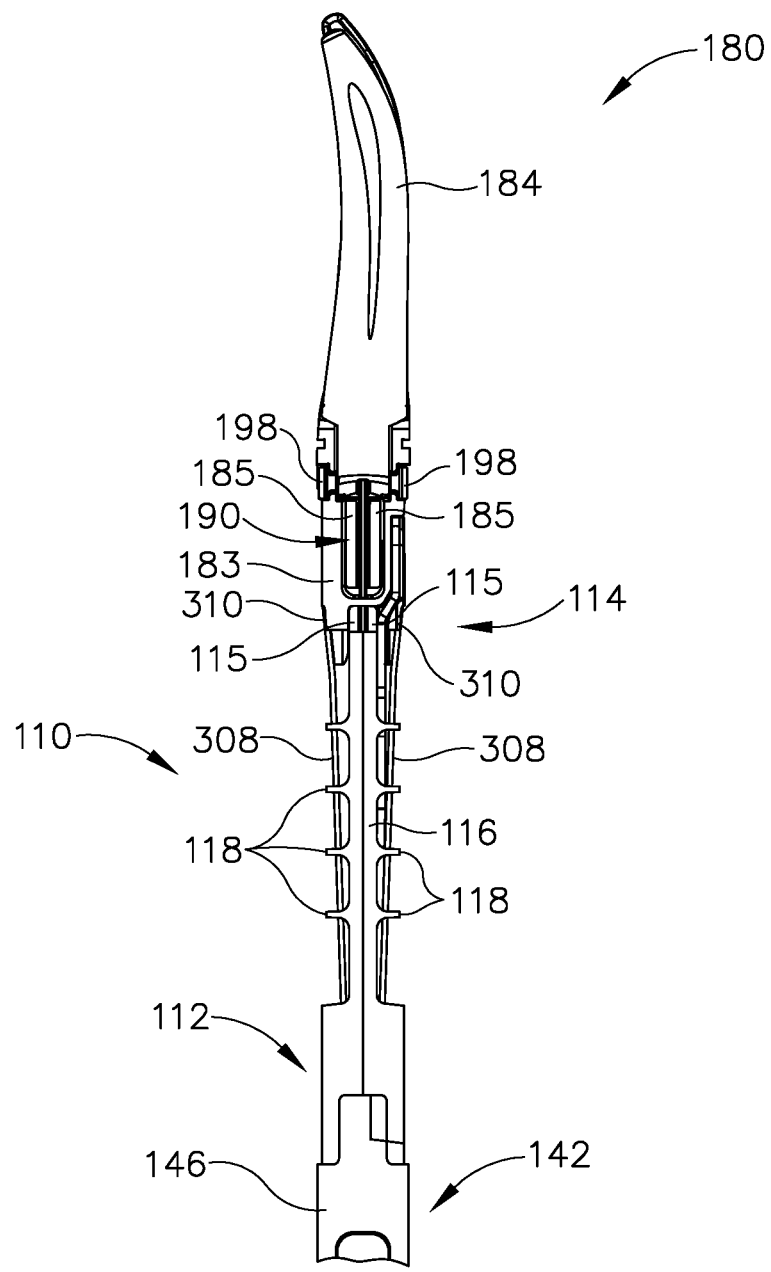
FIG. 10A depicts a top plan view of the end effector and articulation assembly of FIG. 2, where the articulation assembly is in the non-articulated configuration.
Figure 10B:
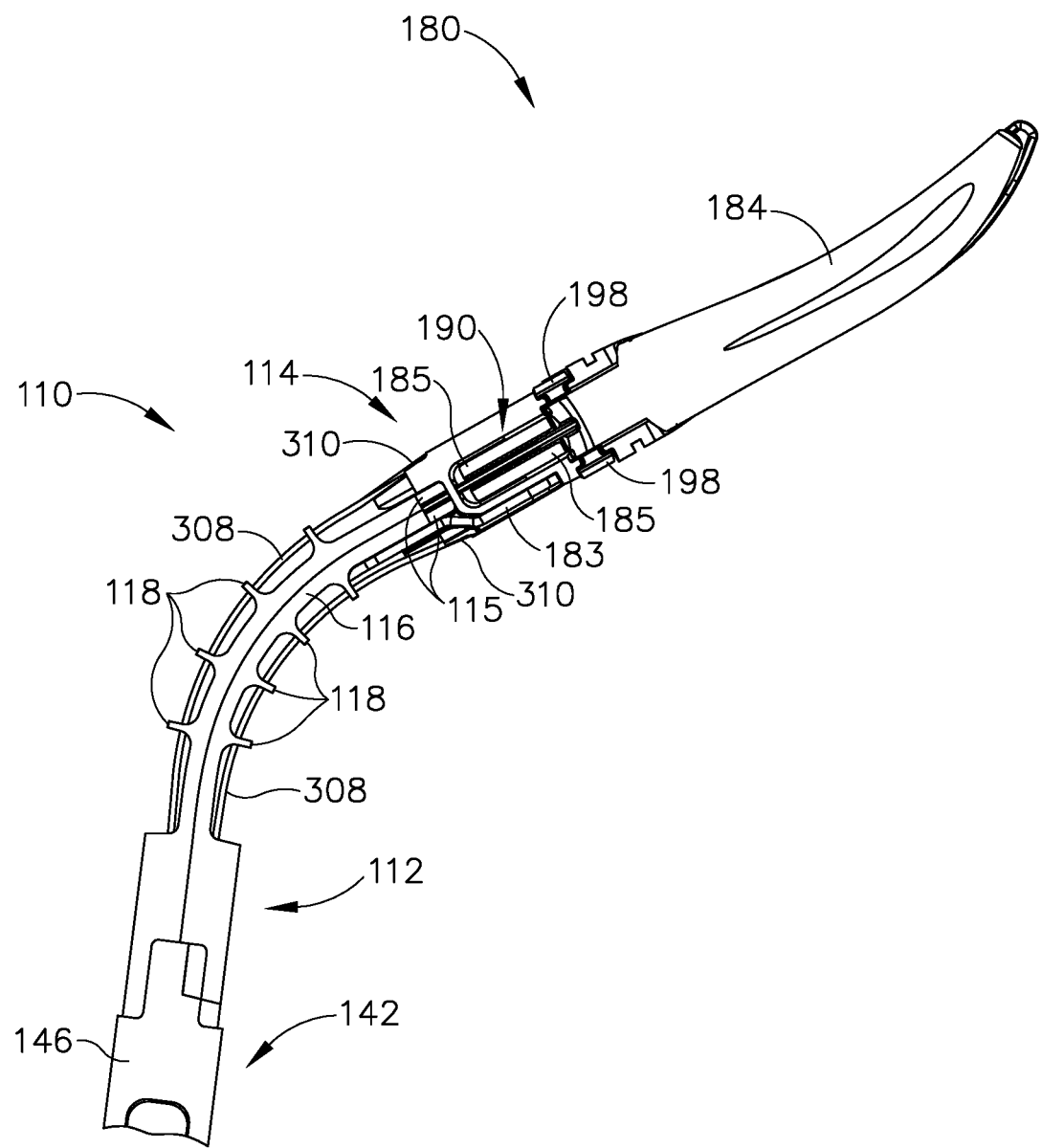
FIG. 10B depicts a top plan view of the end effector and articulation assembly of FIG. 2, where the articulation assembly is in the first articulated configuration.
Figure 10C:
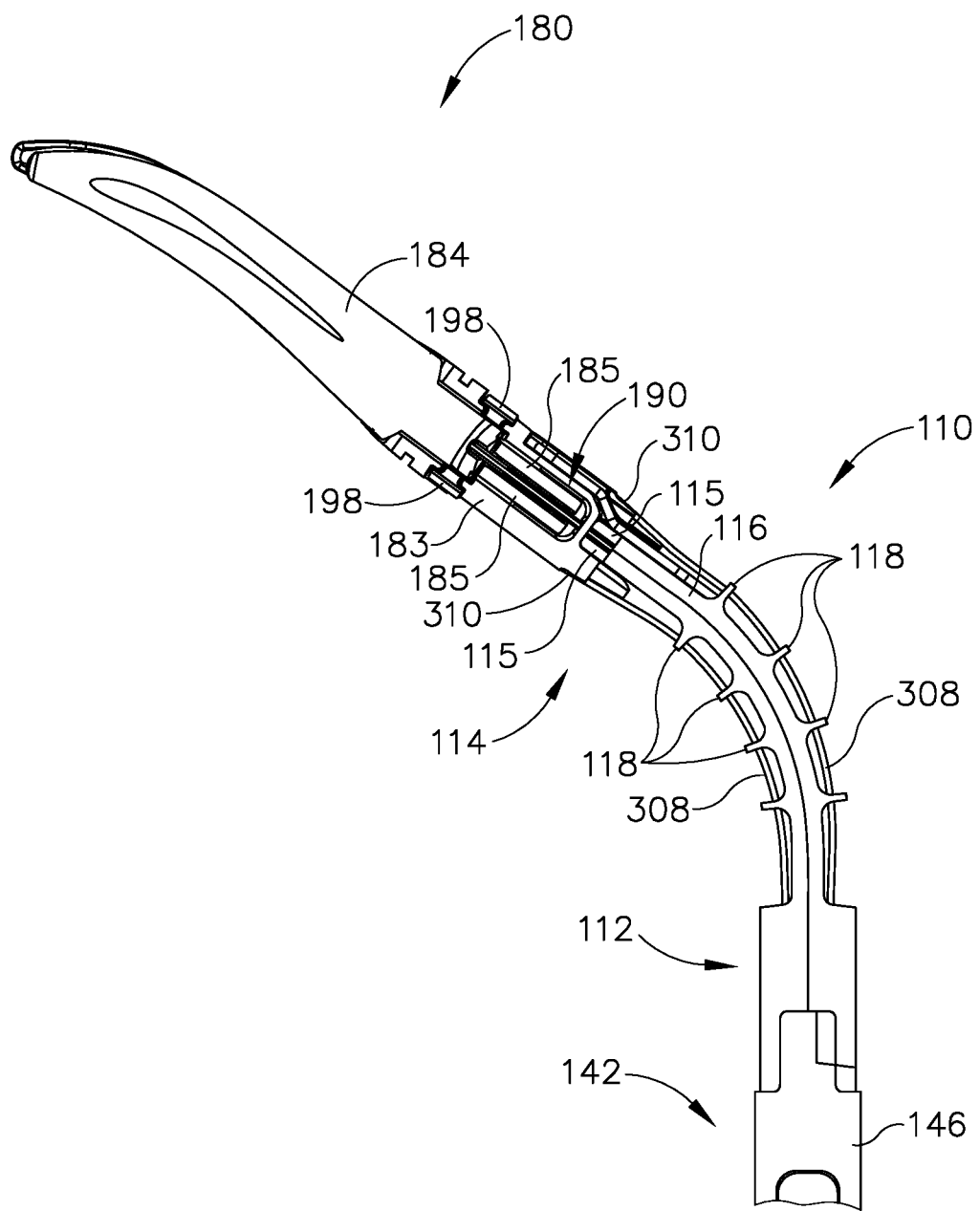
FIG. 10C depicts a top plan view of the end effector and articulation assembly of FIG. 2, where the articulation assembly is in the second articulated configuration.
Figure 11:
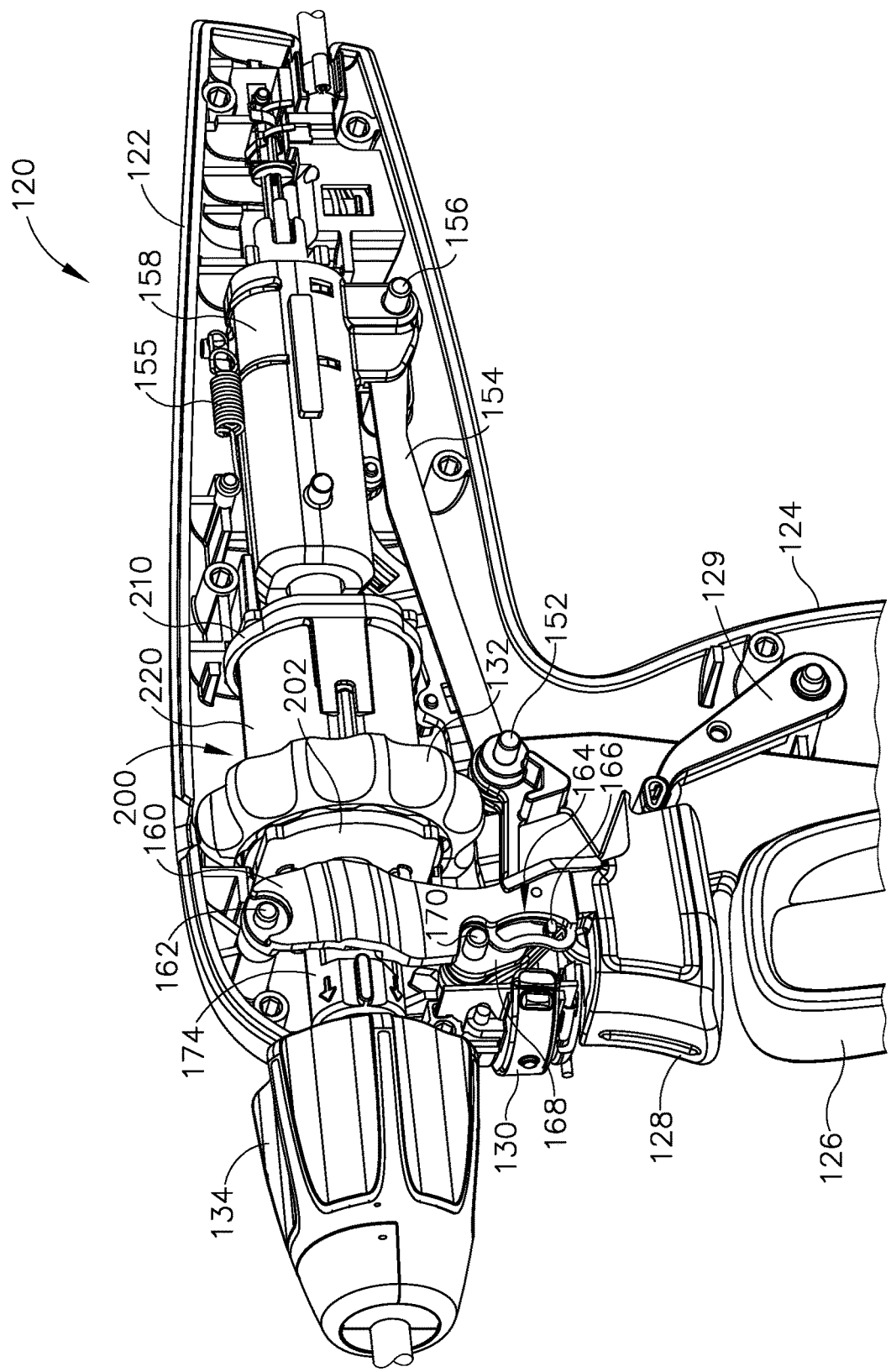
FIG. 11 depicts another perspective view of the handle assembly of FIG. 7A, with selected portions omitted for purposes of clarity.

Flexible members (116) include a plurality of guide members (118) that are configured to slidingly receive a band portion (308) of articulation connector (300). Flexible members (116) and band portions (308) are sufficiently flexible to bend relative to the longitudinal axis defined by shaft assembly (140) (as shown in FIGS. 10B-10C). As best seen in FIGS. 2 and 6, distal coupling portion (310) of articulation connector (300) is fixed to proximal body (183) of a lower jaw (182). As will be described in greater detail below, translation of articulation connectors (300) will drive deflection of end effector (180) relative to the longitudinal axis defined by shaft assembly (140).

Figure 5:
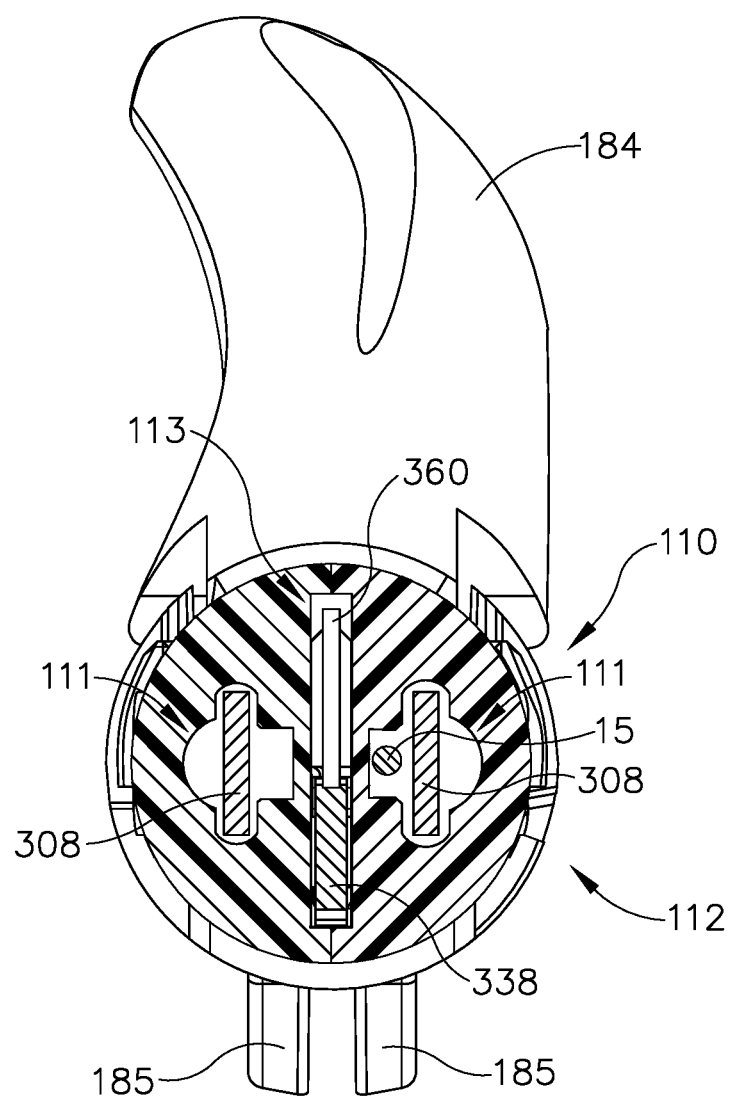
FIG. 5 depicts a cross-sectional rear view of the articulation assembly of FIG. 2, taken along line 5-5 of FIG. 2.

As shown in FIG. 5, rigid proximal portion (112) of articulation section (110) defines a pair of laterally offset pathways (111) and a central pathway (113). Laterally offset pathways (111) are dimensioned to slidably house corresponding band portions (308) of articulation connector (300) and electrical coupling (15); while central pathway (113) is dimensioned to slidably house corresponding portions of knife member (360) and band portion (338) of jaw closure connector (330). Central pathway (313) extends through flexible member (316) and proximal portion (314) to provide a pathway for knife member (360) and band portion (338) of jaw closure connector (330) from shaft assembly (140) to end effector (180). Therefore, knife member (360) and band portion (338) of jaw closure connector (330) are both sufficiently flexible to bend relative to the longitudinal axis defined by shaft assembly (140) (as shown in FIGS. 10B-10C).

As best seen in FIGS. 2-3 and 8A-8C, end effector (180) includes lower jaw (182) pivotally coupled with an upper jaw (184) via pivot couplings (198). Lower jaw (182) includes a proximal body (183) defining a slot (186), while upper jaw (184) includes proximal arms (185) defining a slot (188). Lower jaw (182) also defines a central channel (190) that is configured to receive proximal arms (185) of upper jaw (184), portions of knife member (360), band portion (338) of jaw closure connecter (330), and pin (350). Slots (186, 188) each slidably receive pin (350), which is attached to a distal coupling portion (340) of jaw closure connector (330). As will be described in greater detail below, jaw closure connector (330) is operable to translate within central channel (190) of lower jaw (182). Translation of jaw closure connector (330) drives pin (350). As will be described in greater detail below, because pin (350) is located within both slots (186, 188) and slots (186, 188) are angled relative to each other, pin (350) cams against proximal arms (185) to pivot upper jaw (184) toward and away from lower jaw (182) about pivot couplings (198). Therefore, upper jaw (184) is configured to pivot toward and away from lower jaw (182) about pivot couplings (198) to grasp tissue.

The term "pivot" does not necessarily require rotation about a fixed axis, but may include rotation about an axis that moves relative to end effector (180). Therefore, the axis at which upper jaw (184) pivots about lower jaw (182) may translate relative to both upper jaw (184) and lower jaw (182). Any suitable translation of the pivot axis may be used as would be apparent to one having ordinary skill in the art in view of the teachings herein.

Figure 8A:
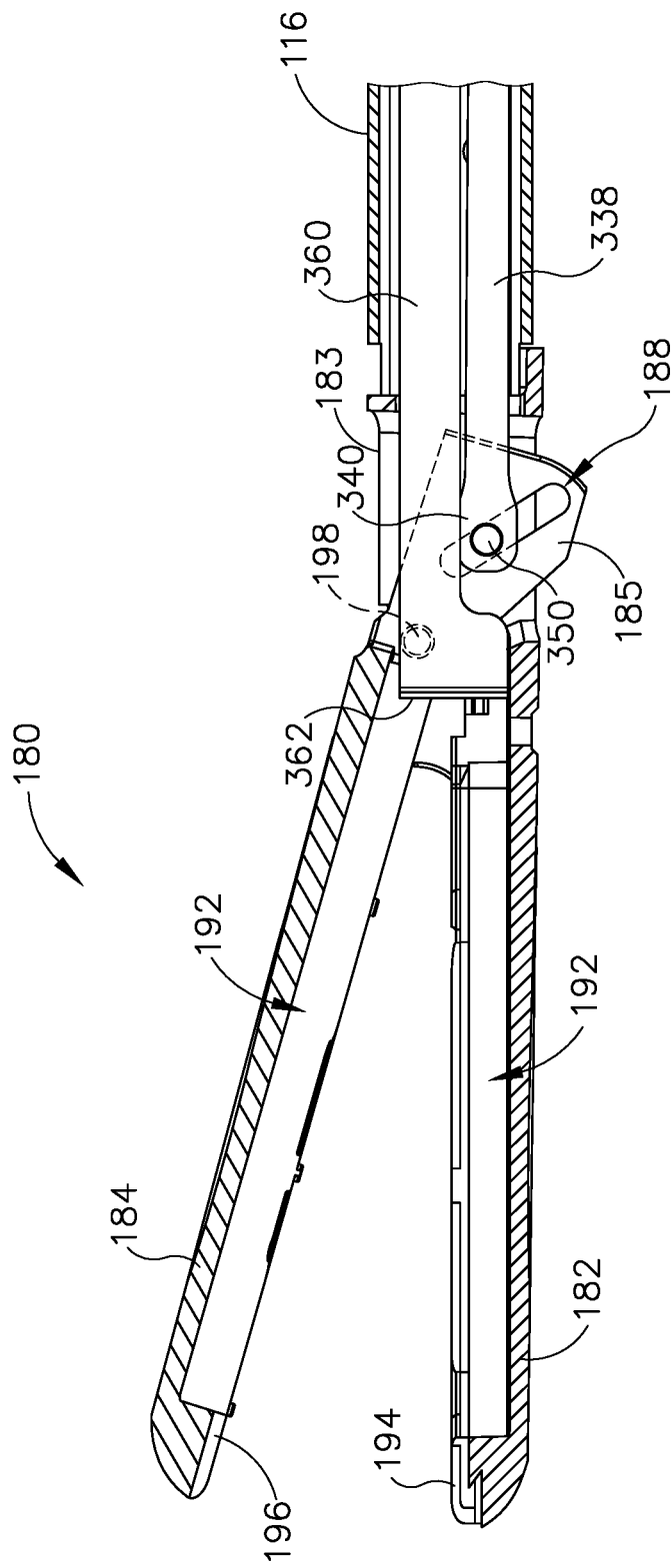
FIG. 8A depicts a cross-sectional side view of the end effector of FIG. 2, where the end effector is in the open and unfired state, taken along line 8-8 of FIG. 6.
Figure 8B:
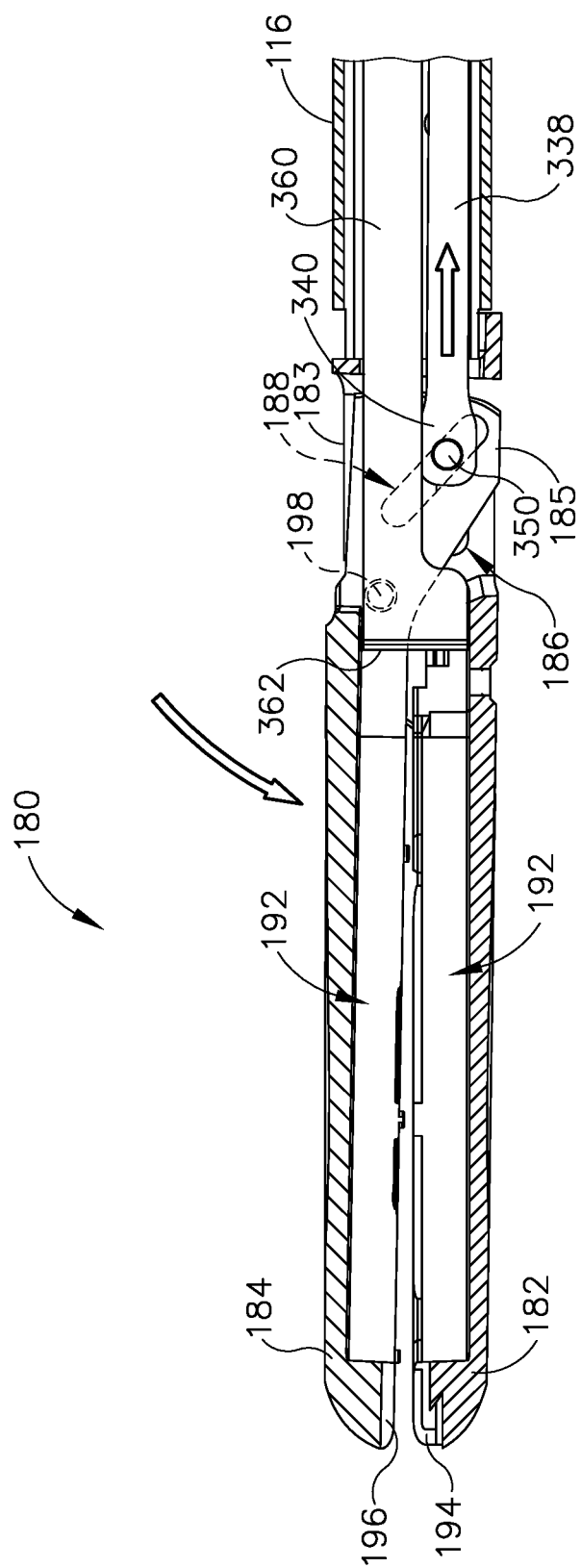
FIG. 8B depicts a cross-sectional side view of the end effector of FIG. 2, where the end effector is in the closed and unfired state, taken along line 8-8 of FIG. 6.
Figure 8C:
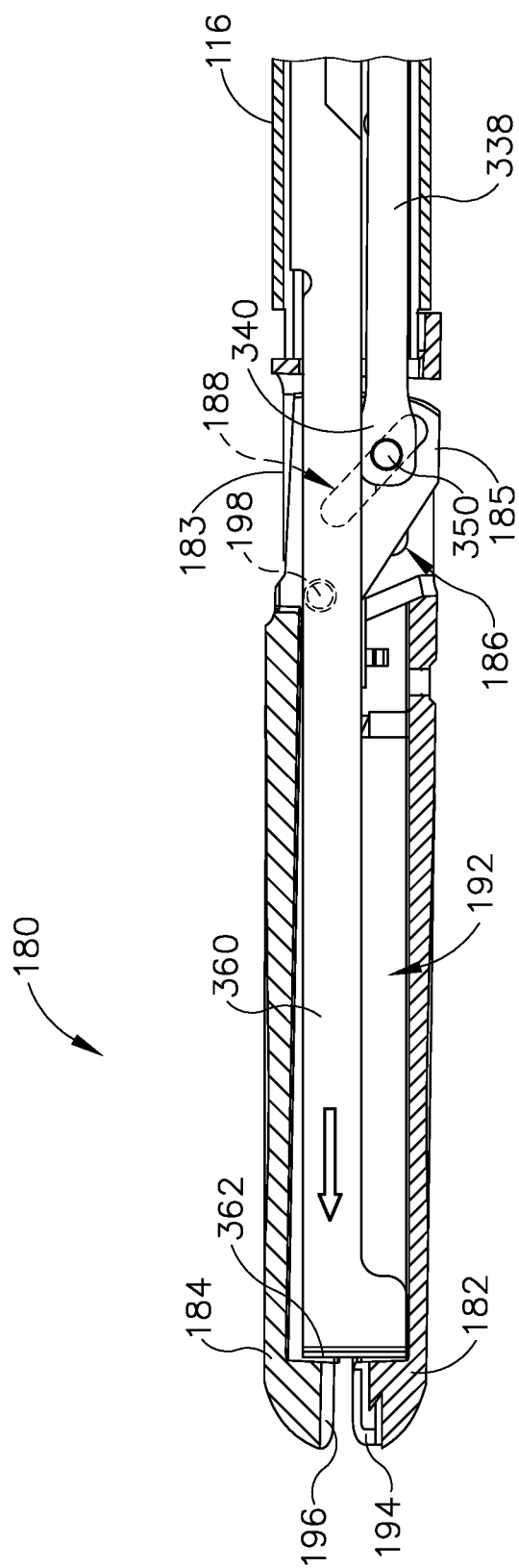
FIG. 8C depicts a cross-sectional side view of the end effector of FIG. 2, where the end effector is in the closed and fired state, taken along line 8-8 of FIG. 6.

Lower jaw (182) and upper jaw (184) also define a knife pathway (192). Knife pathway (192) is configured to slidingly receive knife member (360), such that knife member (360) may be retracted (as shown in FIGS. 8A-8B), and advanced (as shown in FIG. 8C), to cut tissue captured between jaws (182, 184). Lower jaw (182) and upper jaw (184) each comprise a respective electrode surface (194, 196). The power source may provide RF energy to electrode surfaces (194, 196) via electrical coupling (15) that extends through handle assembly (120), shaft assembly (140), articulation assembly (110), and electrically couples with one or both of electrode surfaces (194, 196). Electrical coupling (15) may selectively activate electrode surfaces (194, 196) in response to an operator pressing activation button (130).

FIGS. 7A-8C show an exemplary use of instrument (100) for end effector (180) to grasp, cut, and seal/weld tissue. As described above, and as shown between FIGS. 7A-7B and 8A-8B, jaw closure trigger (126) may be pivoted toward and away from pistol grip (124) and/or body (122) to open and close jaws (182, 184) of end effector (180) to grasp tissue. In particular, handle assembly (120) further includes a yoke (158) that is slidably coupled along proximal portion (144) of shaft assembly (140). Yoke (158) is coupled with rod portion (332) of jaw closure connector (330) such that translation of yoke (158) relative to proximal portion (144) of shaft assembly (140) translates rod portion (332) of jaw closure connector (330) relative to shaft assembly (140). However, rod portion (332) of jaw closure connector (330) is operable to rotate with proximal portion (144) of shaft assembly (140) relative to yoke (158), such that an operator may rotate knob (134) to rotate end effector (180) about the longitudinal axis defined by shaft assembly (140). In other words, rod portion (332) may rotate with shaft assembly (140), independently of yoke (158); yet rod portion (332) is longitudinally fixed with yoke (158). Any suitable coupling mechanism may be used as would be apparent to one having ordinary skill in the art in view of the teachings herein. For instance, yoke (158) may include an internal recess configured to allow rotation of a coupling member relative to yoke (158), while the internal recess of yoke (158) may abut against side walls of the coupling member to longitudinally drive rod portion (332).

As best seen in FIGS. 7A-7C, yoke (158) is coupled to a body (150) of jaw closure trigger (126) via a link (154). Link (154) is pivotally coupled with yoke (158) via pin (156); while link (154) is also pivotally coupled with body (150) of jaw closure trigger (126) via pin (152). Additionally, jaw closure trigger (126) is pivotally coupled with body (122) of handle assembly (120) via pin (170). Therefore, as shown between FIGS. 7A-7B, an operator may pull jaw closure trigger (126) toward pistol grip (124), thereby rotating jaw closure trigger (126) about pin (170). Rotation of jaw closure trigger (126) leads to rotation of link (154) about both pins (152, 156), which in turn drives yoke (158) in the proximal direction along proximal portion (144) of shaft assembly (140). As described above, jaw closure connector (330) extends within shaft assembly (140), articulation section (110), and central channel (190) of lower jaw (182). Additionally, jaw closure connector (330) is also attached to pin (350). Therefore, as seen between FIGS. 8A-8B, proximal translation of yoke (158) leads to proximal translation of pin (350), which in turn cams against slots (188) of proximal arms (185) of upper jaw (184), thereby rotating upper jaw (184) about pivot couplings (198) toward lower jaw (182) such that jaws (182, 184) achieve a closed configuration.

As best seen in FIGS. 7A-7B, yoke (158) is also coupled with a bias spring (155). Bias spring (155) is also coupled to a portion of body (122), such that bias spring (155) biases yoke (158) to the position shown in FIG. 7A (associated with the open configuration of end effector (180) as shown in FIG. 8A). Therefore, if an operator releases jaw closure trigger (126), bias spring (155) will translate yoke (158) to the position shown in FIG. 7A, thereby opening jaws (182, 184) of end effector (180).

As described above, and as shown between FIGS. 7B-7C and 8B-8C, knife trigger (128) may be pivoted toward and away from body (122) and/or pistol grip (124) to actuate knife member (360) within knife pathway (192) of jaws (182, 184) to cut tissue captured between jaws (182, 184). In particular, handle assembly (120) further includes a knife coupling body (174) that is slidably coupled along proximal portion (144) of shaft assembly (140). Knife coupling body (174) is coupled with knife rod (364) of knife member (360) such that translation of knife coupling body (174) relative to proximal portion (144) of shaft assembly (140) translates knife rod (364) and knife member (360) relative to shaft assembly (140). However, knife rod (364) of knife member (360) is operable to rotate with proximal portion (144) of shaft assembly (140) relative to knife coupling body (174), such that an operator may rotate knob (134) to rotate end effector (180) about the longitudinal axis defined by shaft assembly (140). In other words, knife rod (264) may rotate with shaft assembly (140), independently of knife coupling body (174); yet knife rod (264) is longitudinally fixed to knife coupling body (174). Any suitable coupling mechanism may be used as would be apparent to one having ordinary skill in the art in view of the teachings herein. For instance, knife coupling body (174) may include an internal recess that is configured to allow rotation of a coupling member relative to knife coupling body (174), while the internal recess of knife coupling body (174) may abut against side walls of the coupling member to longitudinally drive knife member (360).

As best seen in FIGS. 7B-7C, knife coupling body (174) is coupled to a second pivoting arm (168) via a protrusion (176) of the knife coupling body (174) and a slot (172) defined by second pivoting arm (168). Second pivoting arm (168) is pivotally coupled with body (122) of handle assembly (120) via pin (170). Second pivoting arm (168) is coupled to a first pivoting arm (160) via a protrusion (166) of second pivoting arm (168) and a slot (164) defined by first pivoting arm (160). First pivoting arm (160) is pivotally connected to a pin (162) and is unitarily attached to knife trigger (128). Therefore, as knife trigger (128) pivots toward body (122) and/or pistol grip (124), first pivoting arm (160) pivots about pin (162) in a first angular direction. As first pivoting arm (160) pivots about pin (162), second pivoting arm (168) pivots about pin (170) in a second, opposite, angular direction due to slot (164) actuating protrusion (166). As second pivoting arm (168) pivots about pin (170) in the second angular direction, knife coupling body (174) translates along proximal portion (144) of shaft assembly (140) due to slot (172) actuating protrusion (176) of knife coupling body (174). Because knife coupling body (174) is coupled to knife member (360), knife member (360) translates distally within shaft assembly (140), articulation section (110), and within knife pathway (192) of end effector (180), as best shown between FIGS. 8B-8C. Knife member (360) includes distal cutting edge (362) that is configured to sever tissue captured between jaws (182, 184). Therefore, pivoting knife trigger (128) causes knife member (360) to actuate within knife pathway (192) of end effector (180) to sever tissue captured between jaws (182, 184).

As best seen in FIGS. 7B-7C, knife trigger (128) is biased to the positions shown in FIG. 7A-7B by a bias arm (129). Bias arm (129) may include any suitable biasing mechanism as would be apparent to one having ordinary skill in the art in view of the teachings herein. For instance, bias arm (129) may include a torsion spring. Bias arm (129) is also coupled to a portion of body (122), such that bias arm (129) biases knife trigger (128) to the position shown in FIG. 7A-7B (associated with the knife member (360) in the retracted position). Therefore, if an operator releases knife trigger (128), bias arm (129) returns knife trigger (128) to the position shown in FIGS. 7A-7B, thereby translating knife member (360) toward the retracted position.

With distal cutting edge (362) of knife actuated to the advance position (position shown in FIG. 8C), an operator may press activation button (130) to selectively activate electrode surfaces (194, 196) of jaws (182, 184) to weld/seal severed tissue that is captured between jaws (182, 184).

As described above, and as best shown between FIGS. 9A-10C, rotation of articulation control (132) relative to body (122) of hand assembly (120) will drive deflection of end effector (180) from the longitudinal axis defined by shaft assembly (140) from a non-articulated configuration (FIG. 10A) to an articulated configuration (FIGS. 10B-10C). In particular, as best shown in FIGS. 9A-9C, handle assembly (120) further includes an articulation drive assembly (200). Articulation drive assembly (200) includes a rotatable housing (220) that is unitarily connected to articulation control (132), such that rotation of articulation control (132) relative to body (122) leads to rotation of rotatable housing (220) relative to body (122). Half of rotatable housing (220) is purposely omitted from FIGS. 9A-9C for purposes of clarity.

Rotatable housing (220) and articulation control (132) are rotatably coupled to a distal cap (202) and a proximal cap (210), which are both fixed to body (122) of handle assembly (120). Rotatable housing (220) includes a first internal threading (222) and a second internal threading (224). First internal threading (222) is threaded in an opposite orientation/direction as compared to second internal threading (224).

Additionally, articulation drive assembly (200) includes a first lead screw assembly (230) and a second lead screw assembly (250) slidably coupled along proximal portion (144) of shaft assembly (140). First lead screw assembly (230) and second lead screw assembly (250) each have pins (204) extending through them. Pins (204) are fixed to proximal cap (210) and distal cap (202). Therefore, pins (204) are rotationally fixed relative to body (122) of handle assembly (120). Because pins (204) extend through lead screw assemblies (230, 250), lead screw assemblies (230, 250) are also rotationally fixed relative to body (122) of handle assembly (120). However, first lead screw assembly (230) and second lead screw assembly (250) are slidably attached to pins (204). Therefore, lead screw assemblies (230, 250) may translate, without rotating, along pins (204) and proximal portion (144) of shaft assembly (140) within the confines of rotatable housing (220).

First lead screw assembly (230) includes threading (232) that is configured to mesh with first internal threading (222) of rotatable housing (220). Second lead screw assembly (250) includes threading (252) that is configured to mesh with second internal threading (224) of rotatable housing (220). Because lead screw assemblies (230, 250) are rotationally fixed relative to body (122), and because each lead screw assembly (230, 250) has threading (232, 252) that meshes with internal threading (222, 224) having opposing orientation/direction, rotation of rotatable housing (220) in one direction leads to simultaneous translation of lead screw assemblies (230, 250) in opposing longitudinal directions. In other words, rotation of rotatable housing (220) causes first and second internal threading (222, 224) to cam against threading (232, 252) of lead screw assemblies (230, 250) respectively, such that longitudinal actuating lead screw assemblies (230, 250) in opposite longitudinal directions. For instance, if an operator rotates articulation control (132) and rotatable housing (220) in a first rotational direction, lead screw assemblies (230, 250) will translate away from each other (as shown between FIGS. 9A-9B) due to rotation of internal threading (222, 224) causing contact with threading (232, 252) of lead screw assemblies (230, 250), respectively. However, if an operator rotates articulation control (132) and rotatable housing (220) in a second rotational direction, lead screw assemblies (230, 250) will translate toward each other (as shown between FIGS. 9A and 9C) due to rotation of internal threading (222, 224) causing contact with threading (232, 252) of lead screw assemblies (230, 250), respectively.

As will be described in greater detail below, each lead screw assembly (230, 250) is coupled with a respective rod portion (302) of articulation connectors (300) such that translation of lead screw assemblies (230, 250) relative to proximal portion (144) of shaft assembly (140) translates rod portions (302) of articulation connectors (300) relative to shaft assembly (140). However, rod portions (302) of articulation connectors (300) are operable to rotate with proximal portion (144) of shaft assembly (140) relative to their respective lead screw assemblies (230, 250), such that an operator may rotate knob (134) to rotate end effector (180) about the longitudinal axis defined by shaft assembly (140). In other words, articulation connectors (300) may rotate with shaft assembly (140) independently of lead screw assemblies (230, 250), yet articulation connectors (300) are longitudinally fixed with lead screw assemblies (230, 250). Any suitable coupling mechanism may be used as would be apparent to one having ordinary skill in the art in view of the teachings herein. For instance, lead screw assemblies (230, 250) may each include an internal recess configured to allow rotation of a coupling member relative to lead screw assemblies (230, 250), while the internal recess of lead screw assemblies (230, 250) may abut against side walls of the coupling member to longitudinally drive articulation connection (300).

As mentioned above, articulation connector (300) includes rod portions (302) that are configured to longitudinally translate relative to shaft assembly (140) by coupling with lead screw assemblies (230, 250). As also described above, each articulation connector (300) include a flexible band portion (308) slidably disposed within articulation section (110) of instrument (100); while articulation connectors (300) each include a distal coupling portion (310) fixed to proximal body (183) of lower jaw (182). Distal coupling portion (310) may be fixed to proximal body (183) of lower jaw (182) through any suitable means known to a person having ordinary skill in the art in view of the teachings herein, such as welding. As also mentioned above, articulation section (110) also includes flexible members (116) that are configured to bend relative to the longitudinal axis defined by the shaft assembly (140) to allow end effector (180) to deflect relative to the longitudinal axis defined by shaft assembly (140).

In an exemplary use, an operator may rotate articulation control (132) and rotatable housing (220) in a first rotational direction such that lead screw assemblies (230, 250) translate away from each other (as shown between FIGS. 9A-9B), as described above. Because lead screw assemblies (230, 250) are each coupled to a respective articulation connector (300), each articulation connector (300) translates with its respective lead screw assembly (230, 250). Therefore, articulation connectors (300) translate in opposing directions in response to rotation of articulation control (131) and rotatable housing (220). As described above, articulation connectors (300) are attached to proximal body (183) of lower jaw (182) via distal coupling portions (310). In particular, distal coupling portion (310) of each articulation connector (300) is attached to an opposite side of proximal body (183) of lower jaw (182). As best shown in FIG. 10B, opposing translation of articulation connectors (300) causes one articulation connector (300) to drive end effector (180) proximally, while causing another articulation connector (300) drive end effector (180) distally, thereby articulating end effector (180) and flexible member (116) of articulation section (110) to a first articulated configuration. Band portion (348) and portions of knife member (360) within central pathway (113) are also flexible to bend with flexible member (116). The degree to which end effector (180) articulates relative to the longitudinal axis defined by shaft assembly (140) may be determined by the longitudinal distance lead screw assemblies (230, 250) travel away from each other compared to their positions shown in FIG. 9A. Therefore, an operator may choose the degree at which end effector (180) articulates based on the rotational displacement of articulation control (132) from its home position shown in FIG. 9A.

Additionally, an operator may rotate articulation control (132) and rotatable housing (220) in a second rotational direction such that lead screw assemblies (230, 250) translate toward each other (as shown between FIGS. 9A and 9C). Because lead screw assemblies (230, 250) are each coupled to a respective articulation connector (300), each articulation connector (300) translates with its respective lead screw assembly (230, 250). Therefore, articulation connectors (300) translate in opposing directions. As best shown in FIG. 10C, translation of articulation connectors (300) leads to end effector (180) being driven to a second articulated configuration. As described above, articulation connectors (300) are attached to a proximal body (183) of lower jaw (182) via distal coupling portions (310). In particular, distal coupling portion (310) of each articulation connector (300) is attached to an opposite side of proximal body (183) of lower jaw (182). As best shown in FIG. 10C, opposing translation of articulation connectors (300) causes one articulation connector (300) to drive end effector (180) proximally, while causing another articulation connector (300) to drive end effector (180) distally, thereby articulating end effector (180) and flexible member (116) of articulation section (110) to a second articulated configuration.

II. EXEMPLARY LEAD SCREW ASSEMBLY

As described above, lead screw assemblies (230, 250) may couple with articulation connectors (300) such that articulation connectors (300) may translate with lead screw assemblies (230, 250); yet articulation connectors (300) may also rotate relative to selected portions of lead screw assemblies (230, 250). Therefore, articulation connectors (300) may longitudinally actuate relative to shaft assembly (140) via longitudinal actuation of lead screw assemblies (230, 250); but articulation connectors (300) may also rotate with shaft assembly (140) relative to lead screw assemblies (230, 250) about the longitudinal axis defined by shaft assembly (140) without longitudinally actuating lead screw assemblies (230, 250).

As also described above, lead screw assemblies (230, 250) are slidably coupled along proximal portion (144) of shaft assembly (140). In some alternative articulation drive assemblies, lead screw assemblies (230, 250) are each formed as a respective single, unitary piece, and therefore are assembled by being longitudinally inserted through either the proximal or distal end of shaft assembly (140) to rotatably couple with articulation connectors (300) and to slidingly couple with shaft assembly (140). For instance, an operator may assemble such alternative lead screw assemblies (230, 250) by inserting the proximal end of proximal portion (144) through a shaft through hole defined by lead screw assembly (230, 250), and then slide lead screw assembly (230, 250) along the length of proximal portion (144) until lead screw assembly (230, 250) is positioned adjacent to slot (145) corresponding to a respective articulation connector (300). Then, lead screw assembly (230, 250) would be suitably coupled with articulation connector (300) through any suitable means known to a person having ordinary skill in the art in view of the teachings herein, such as longitudinal translation of either articulation connector (300) or lead screw assembly (230, 250) into a snap fitting or an interference fit with each other. However, assembling such alternative lead screw assemblies (230, 250) via longitudinal insertion over shaft assembly (140) may increase the tolerance stack of the overall articulation drive assembly (200) and/or articulation connectors (300). Therefore, it may be desirable to reduce the tolerance stack involved in assembly articulation drive assembly (200) to increase the precision of articulation capabilities of articulation drive (200).

The present example includes lead screw assemblies (230, 250) that are configured to enable assembly to shaft assembly (140) without having to longitudinally slide lead screw assemblies (230, 250) through the proximal or distal end of shaft assembly (140); or having to longitudinally slide lead screw assemblies (230, 250) to couple with articulation connectors (300). In other words, as will be described in greater detail below, lead screw assemblies (230, 250) of the present example may be slidably coupled with external sheath (146) and rotatably coupled with articulation connectors (300) at a location directly adjacent to corresponding slots (145) of shaft assembly (140), therefore eliminating the requirement of longitudinally sliding lead screw assembly (230, 250) from one end of external sheath (146) of shaft assembly (140) toward the corresponding slot (145) associated with the corresponding articulation connector (300) during assembly. This may reduce the tolerance stack of articulation drive assembly (200) when coupling lead screw assemblies (230, 250) with corresponding articulation connectors (300).

Figure 12:
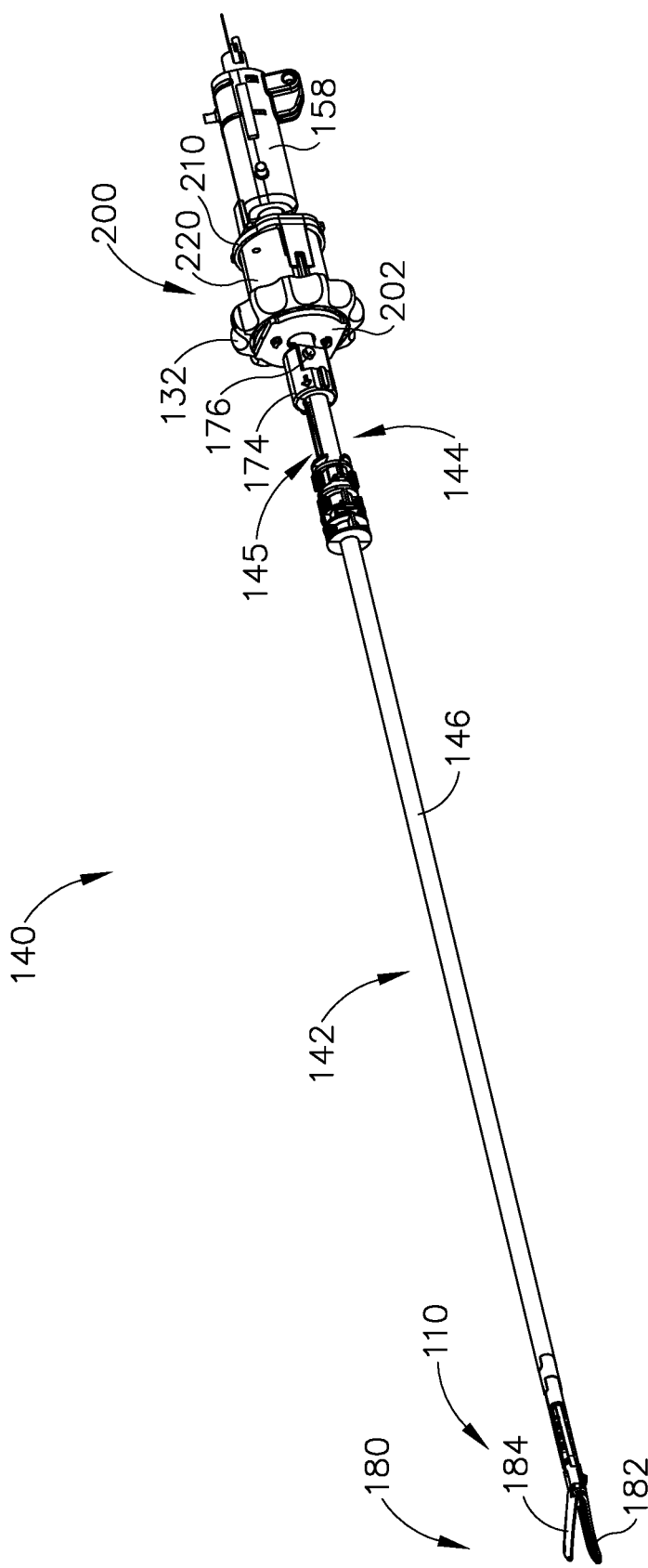
FIG. 12 depicts a perspective view of the shaft assembly of FIG. 4, the articulation assembly of FIG. 2, and the end effector of FIG. 2.
Figure 13:
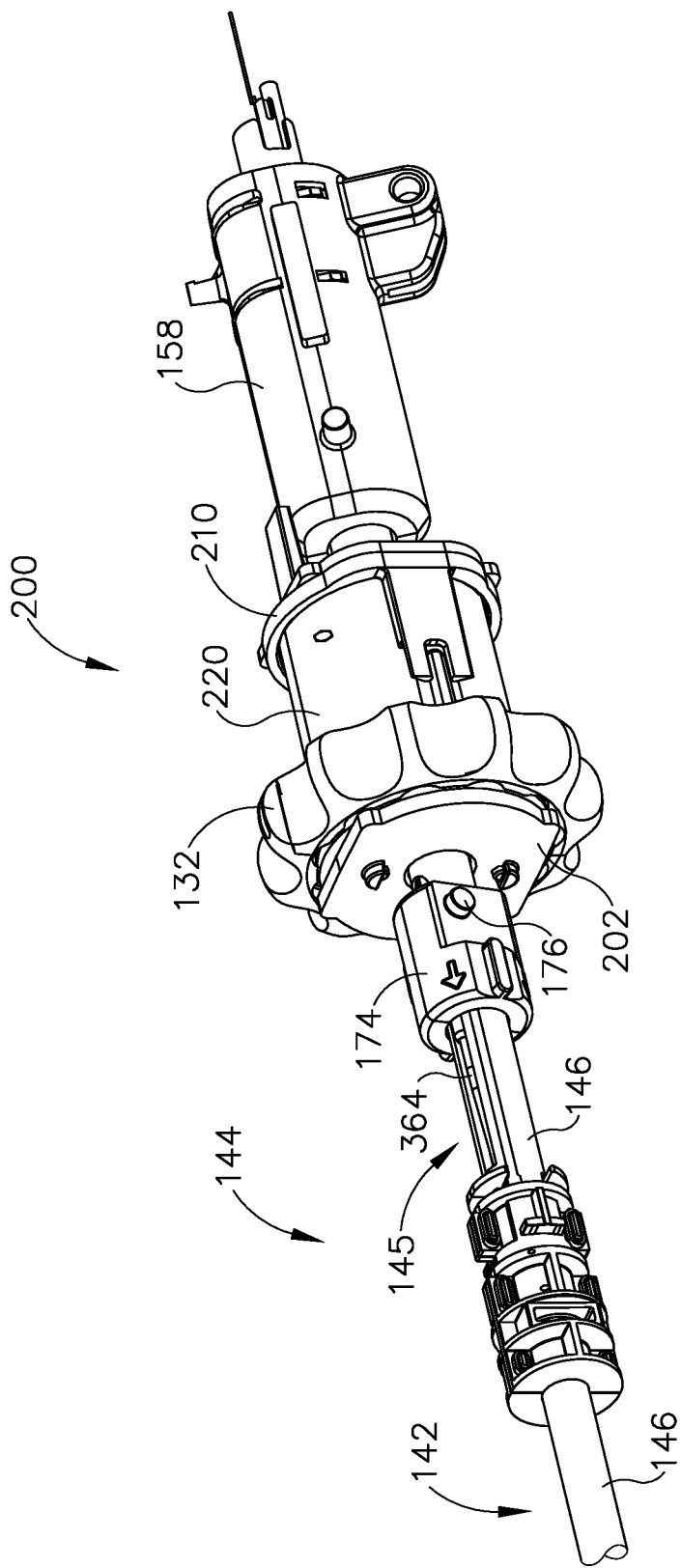
FIG. 13 depicts a perspective view of a proximal portion of the shaft assembly of FIG. 4.
Figure 14:
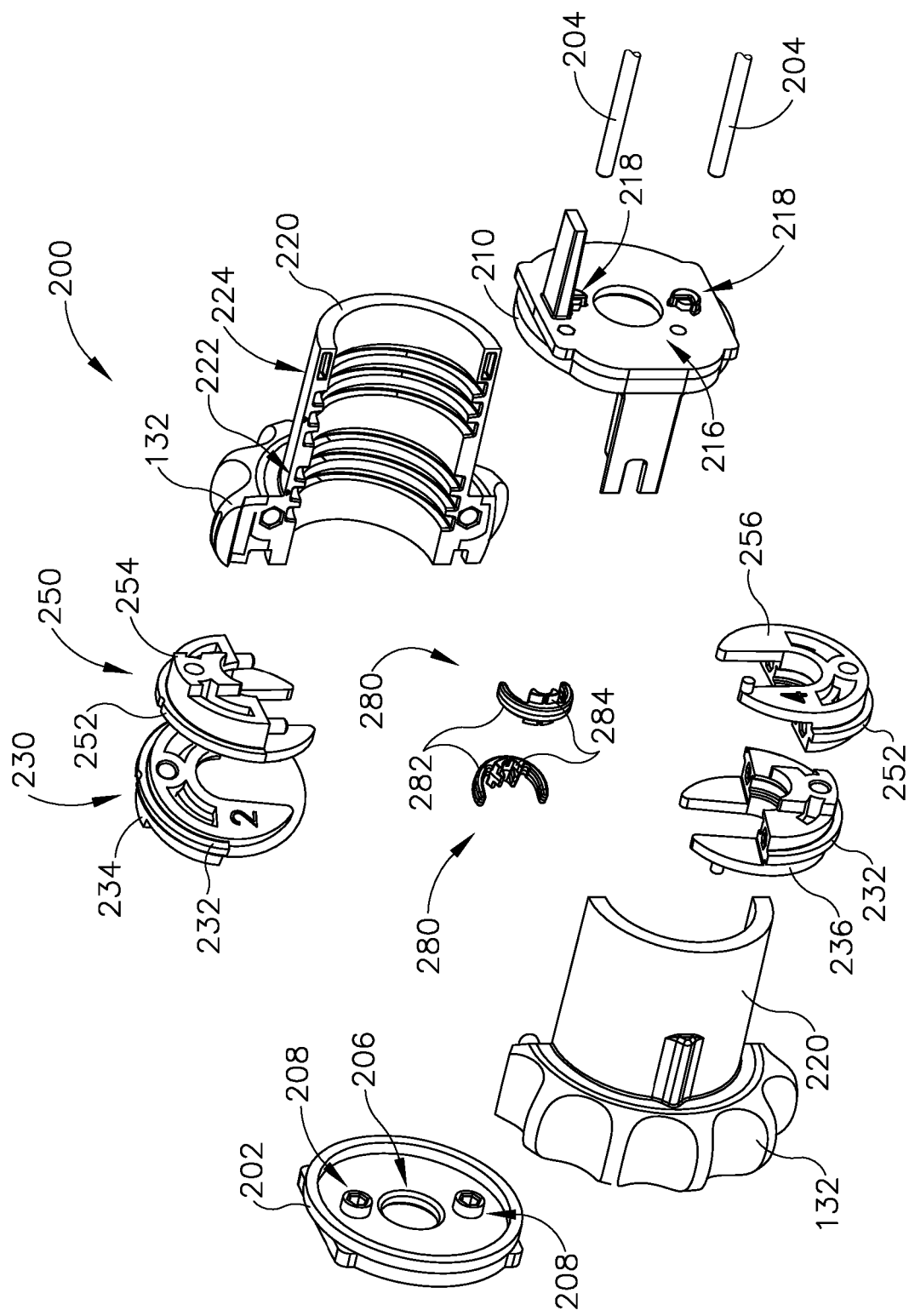
FIG. 14 depicts an exploded perspective view of an exemplary articulation drive of the shaft assembly of FIG. 4.
Figure 15:
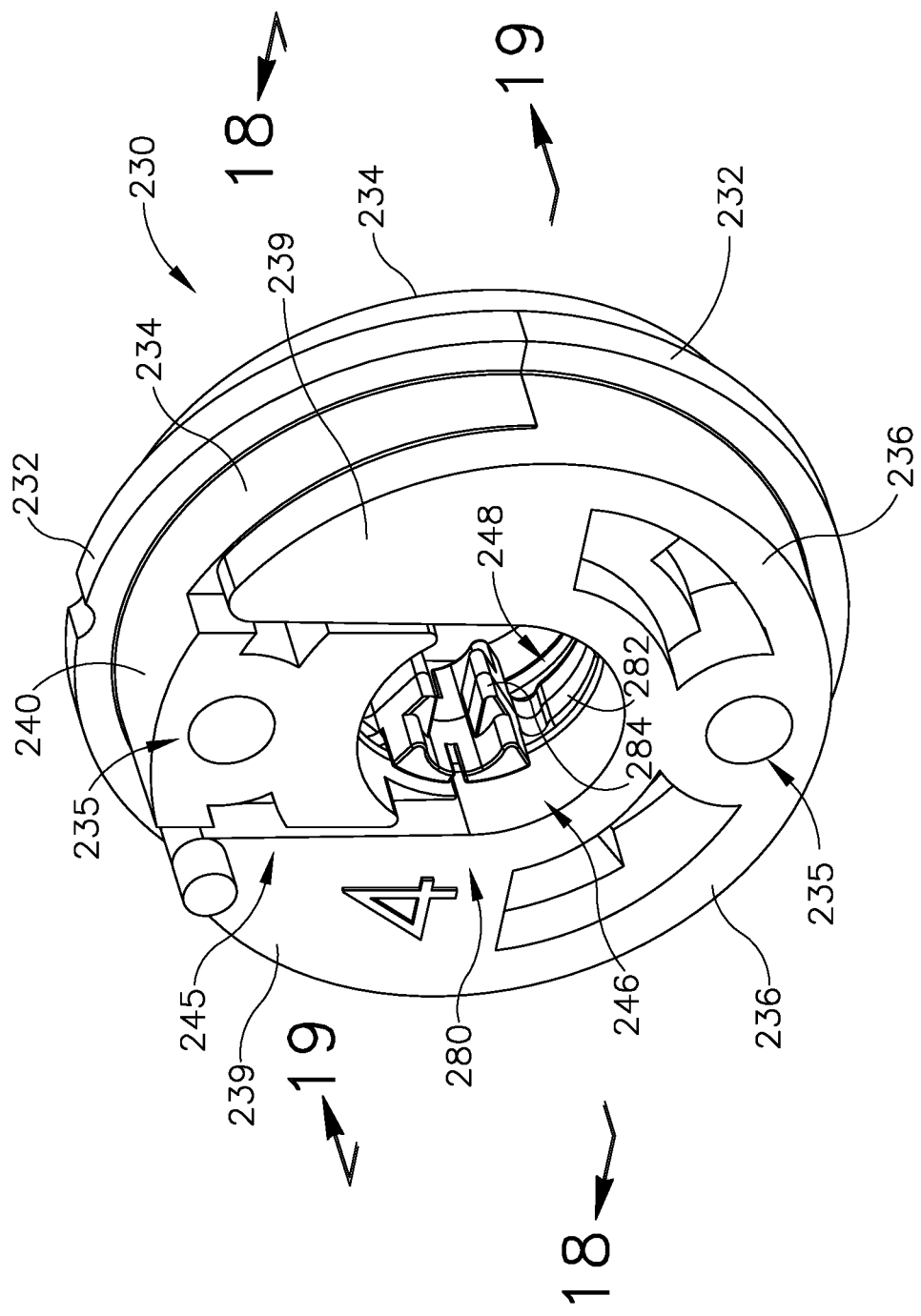
FIG. 15 depicts a perspective view of an exemplary lead screw assembly of the articulation drive of FIG. 14.
Figure 16:
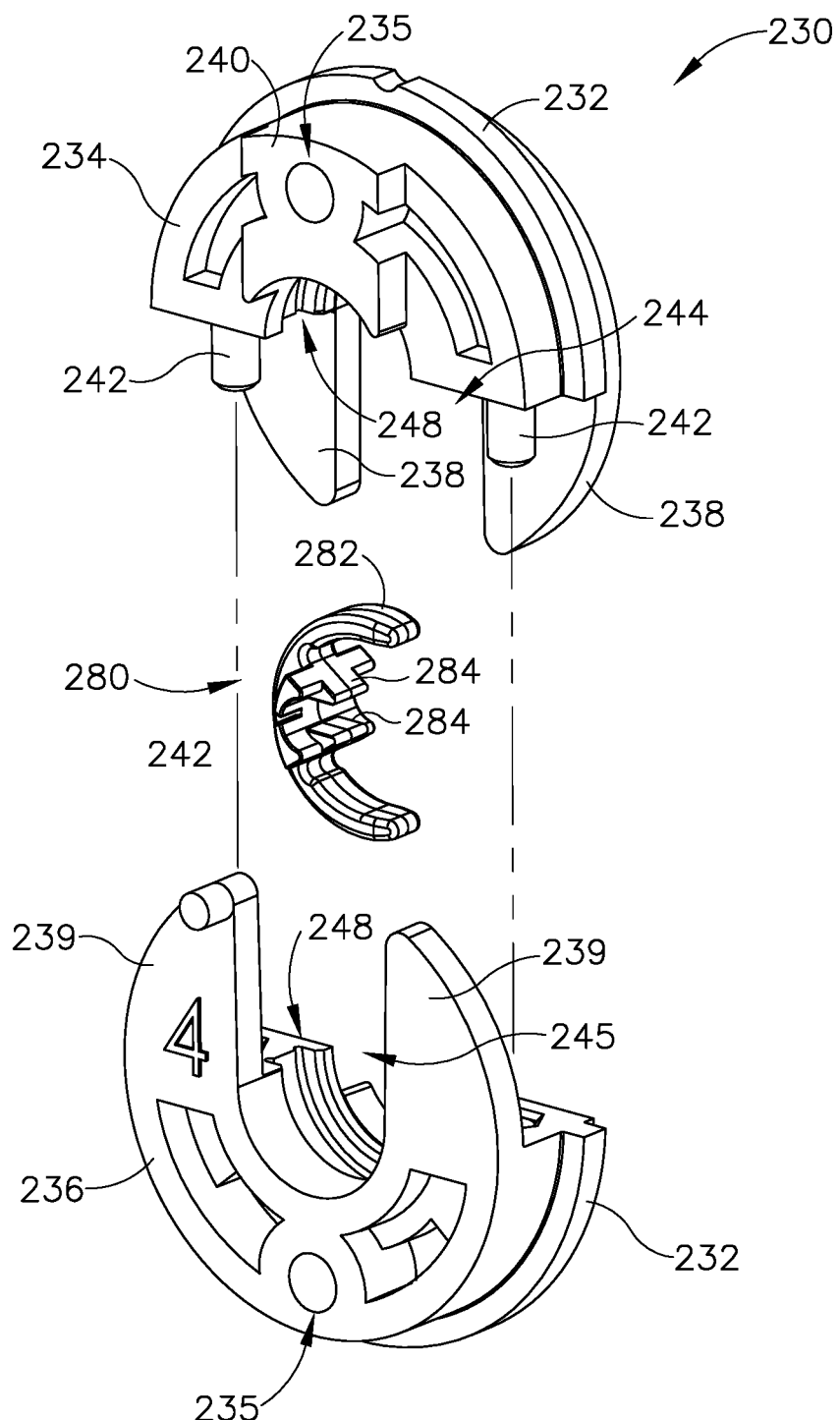
FIG. 16 depicts an exploded perspective view of the lead screw assembly of FIG. 15.
Figure 17:
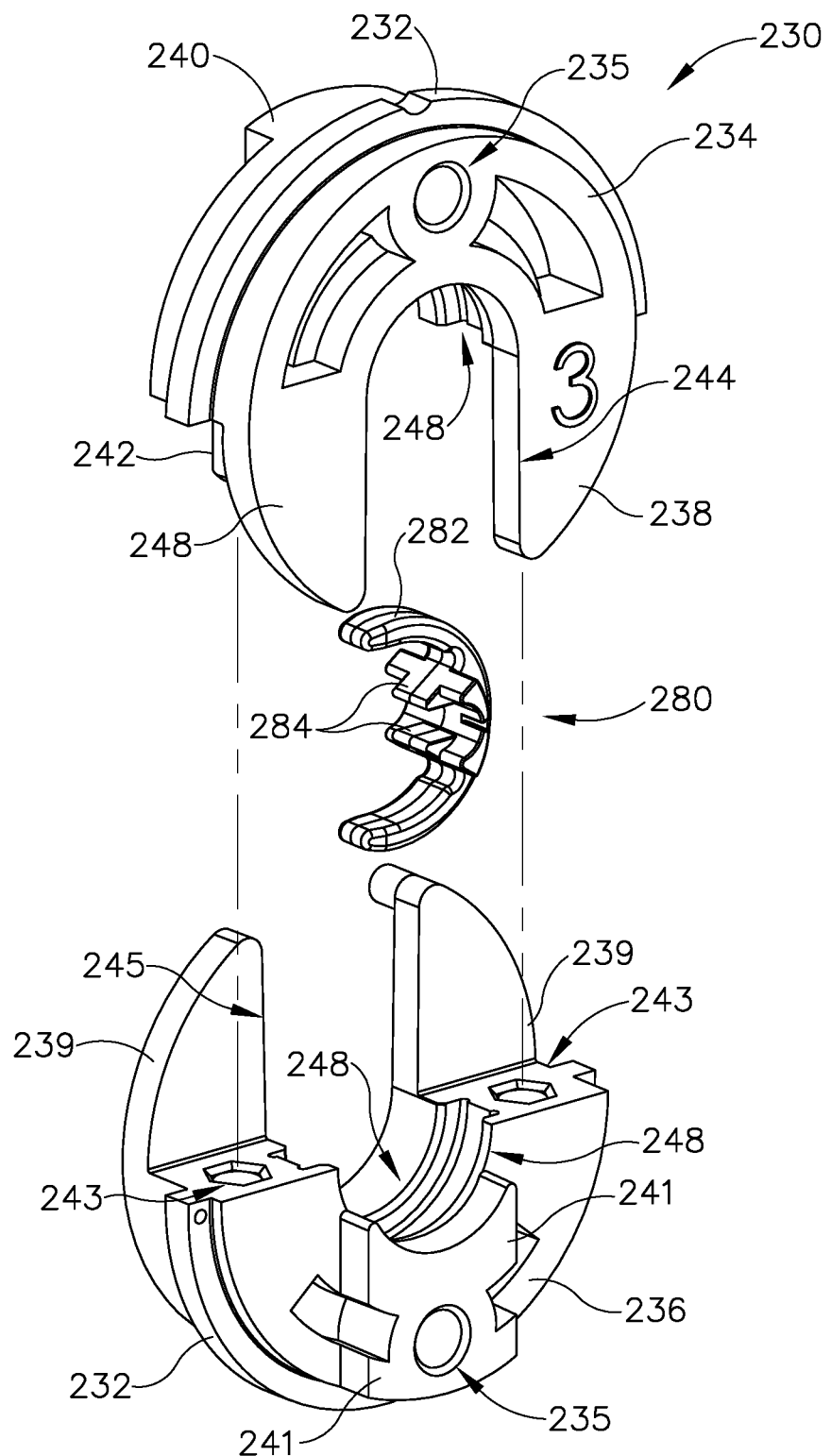
FIG. 17 depicts another exploded perspective view of the lead screw assembly of FIG. 15.

FIG. 12 shows shaft assembly (140), yoke (158), articulation drive assembly (200), knife coupling body (174), articulation section (110), and end effector (180) properly assembled, while FIG. 13 shows proximal portion (144) of shaft assembly (140), yoke (158), articulation drive assembly (200), and knife coupling body (174). As described above, shaft assembly (140) is coupled with articulation drive assembly (200). In the present example, as described above, articulation drive assembly (200) includes distal cap (202), proximal cap (210), articulation control (32), rotatable housing (220), first lead screw assembly (230), and second lead screw assembly (250). Rotatable housing (220) is rotatably coupled to proximal cap (210) and distal cap (202), while caps (202, 210) are fixed to body (122) of handle assembly (120). As best seen in FIG. 14, rotatable housing (220) and articulation control (132) are split into halves, which may be coupled with each other in any suitable manner apparent to one having ordinary skill in the art in view of the teachings herein. It should be understood that halves of rotatable housing (220) couple with each other to cooperatively define first and second internal threading (222, 224).

Proximal cap (210) defines a shaft through hole (216) and pin holes (218). Shaft through hole (216) is dimensioned to receive shaft assembly (140) while pin holes (218) are dimensioned to receive pins (204). Similarly, distal cap (202) defines a shaft through hole (206) and pin holes (208). Shaft through hole (206) is dimensioned to receive shaft assembly (140) while pin holes (208) are dimensioned to receive pins (204). As described above, pins (204) are configured to ratably fix lead screw assemblies (230, 250) relative to body (122) of handle assembly (120).

Lead screw assemblies (230, 250) in the present example each include a first half (234, 254) and a second half (236, 256), respectively. As will be described in greater detail below, first half (234, 254) and second half (236, 256) of respective lead screw assemblies (230, 250) are configured to couple with each other such that lead screw assemblies (230, 250) may be slidably coupled with external sheath (146) of shaft assembly (140) as well as rotatably coupled with articulation connectors (300) via lateral attachment. The term "slidably coupled" means that two objects are attached to each other or otherwise coupled together with the capability of sliding relative to each other. Thus, lead screw assemblies (230, 250) are capable of sliding relative to external sheath (146) of shaft assembly (140). It should also be understood that the term "rotatably coupled" means that two objects are attached to each other or otherwise coupled together with the capability of rotating relative to each other. Thus, articulation connectors (300) are capable of rotating relative to lead screw assemblies (230, 250). In the present examples, lead screw assemblies (230, 250) translate longitudinally but do not rotate during operation of instrument (100).

FIGS. 15-19 show first lead screw assembly (230). While first lead screw assembly (230) is shown in greater detail, it should be understood that second lead screw assembly (250) may be substantially similar to first lead screw assembly (230), except that threading (252) of second lead screw assembly (250) is oriented in an opposite direction as compared to threading (232) of first lead screw assembly (230) for reasons described above.

First half (234) of lead screw assembly (230) includes a portion of threading (232), a pair of laterally spaced projections (238), a central projection (240), and a pair of coupling posts (242). Laterally spaced projections (238) define an open slot (244). Open slot (244) is dimensioned to receive a central projection (241) of second half (236) when first half (234) and second half (236) are properly coupled. Additionally, open slot (244) and open slot (245) of second half (236) together define a shaft through hole (246) when properly coupled such that first lead screw assembly (230) may slidably attach around external sheath (146) of shaft assembly (140). First half (234) further defines a pin hole (235) that is configured to slidably receive pin (204), as described in greater detail above. Additionally, first half (234) also defines a portion of cavity (248). As will be described in greater detail below, cavity (248) is dimensioned to receive a coupling member (280) such that coupling member (280) may rotate within the confines of cavity (248) but longitudinally translate with lead screw assembly (230).

Similar to first half (234) of lead screw assembly (230), second half (236) includes a portion of threading (232), a pair of laterally spaced projections (239), and central projection (240). Laterally spaced projections (239) define open slot (245). Similar to slot (244) of first half (234), slot (245) of second half (236) is dimensioned to receive central projection (240) of first half (234). Second half (236) also defines a pin hole (235) that is configured to slidably receive pin (204), as described in greater detail above. Additionally, second half (236) also defines a portion of cavity (248). However, instead of coupling posts (242), second half (236) defines a pair of post holes (243) that are configured to receive coupling posts (242) such that first half (234) and second half (236) fixedly couple with each other. Post holes (243) and coupling posts (242) may couple with each other through any suitable means as will be apparent to one having ordinary skill in the art in view of the teachings herein. For example, post holes (243) and coupling posts (242) may couple with each other via an interference fit, a latch, through adhesives, etc.

When properly coupled, threading (232) from first half (234) and second half (236) are aligned with each other to form a continuous and aligned threading (232). Therefore, when first half (234) and second half (236) are properly coupled and assembled within rotatable housing (220) of articulation drive assembly (200), threading (232) will cam against first internal threading (222) in response to rotation of rotatable housing (220) to longitudinally translate lead screw assembly (230) relative to shaft assembly (140). Open slots (245, 244) defined by laterally spaced projections (239, 238) housing central projection (240, 241), respectively, may help first half (234) and second half (236) maintain the continuously aligned nature of threading (232) in response to forces provided by the camming action of internal threading (222) of rotatable housing (220).

Figure 18:
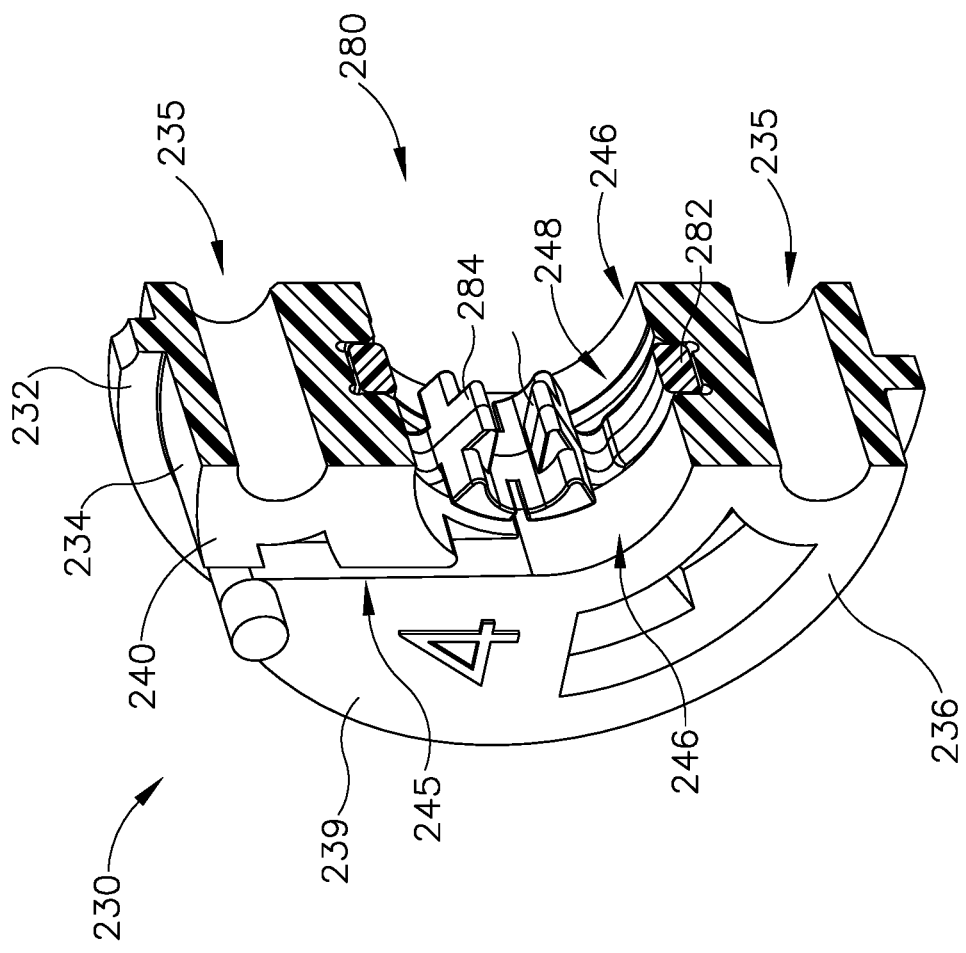
FIG. 18 depicts a cross-sectional perspective view of the lead screw assembly of FIG. 15, taken along line 18-18 of FIG. 15.
Figure 19:
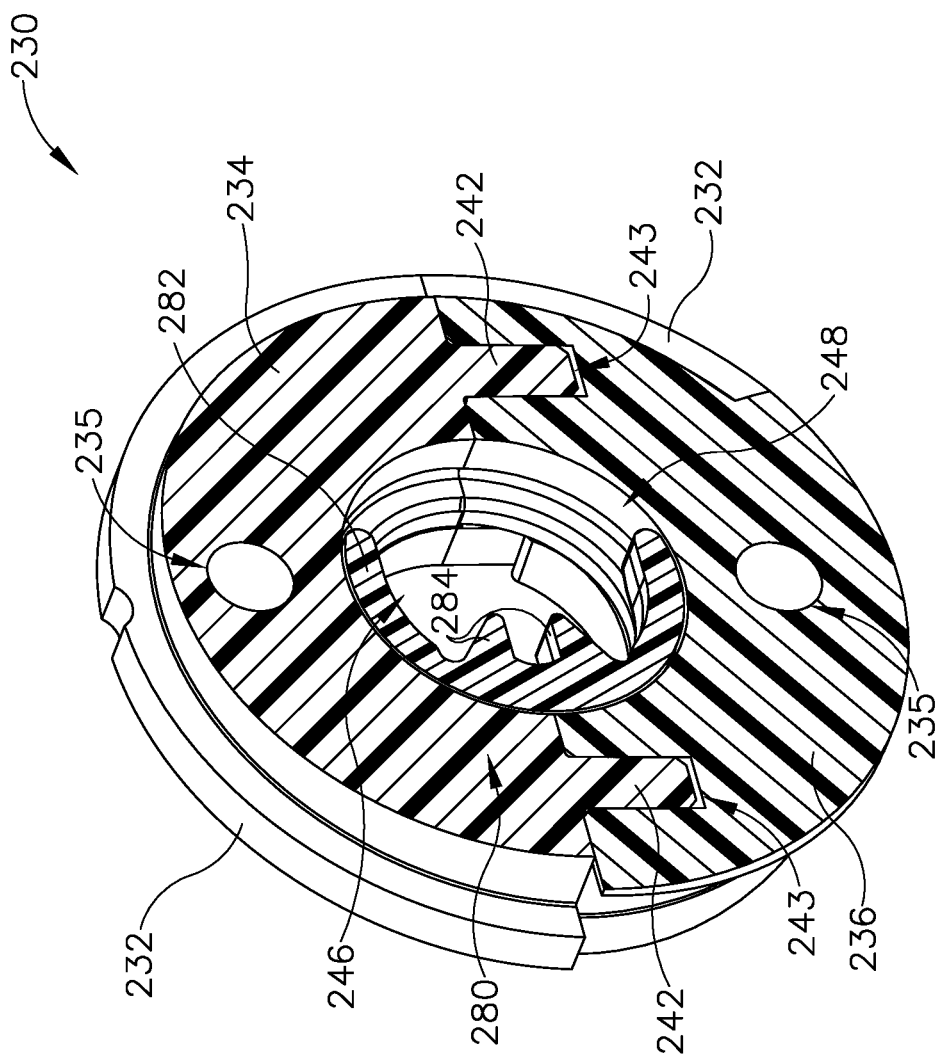
FIG. 19 depicts a cross-sectional perspective view of the lead screw assembly of FIG. 15, taken along line 19-19 of FIG. 15.

As best seen in FIGS. 18-19, first half (234) and second half (236) cooperatively define cavity (248) when properly coupled. Cavity (248) is dimensioned to house coupling member (280). Coupling member (280) includes an arched body (282) and coupling arms (284). Arched body (282) is dimensioned to be housed within cavity (248) such that coupling member (280) may rotate within the confines of cavity (248) about the longitudinal axis defined by external sheath (146) of shaft assembly (140); but also such that coupling member (280) longitudinally travels with lead screw assembly (230) relative to shaft assembly (140). In other words, side walls of cavity (248) abut against arched body (282) of coupling member (280) to translate coupling member (280) in response to translation of first and second half (234, 236) in response to rotation of rotatable housing (220). However, arched body (282) may still rotate along a circumference defined by cavity (248). Additionally, arched body (282) circumferentially extends around the perimeter of cavity (248) to a length such that coupling member (280) may not laterally/radially translate within cavity (248).

Coupling arms (284) extend radially inwardly toward the center of shaft through hole (246). Coupling arms (284) may be resilient in nature such that coupling arms (284) may flex. Of course, coupling arms (284) may alternatively be rigid as to resist flexing. As will be described in greater detail below, coupling arms (284) are configured couple with a pull tube (370), which may further be coupled to articulation connector (300). Coupling arms (284) are configured to couple with pull tube (370) such that pull tube (370), and therefore articulation connector (300), translates and rotates with coupling member (280). In other words, coupling arms (284) are configured to fix coupling member (280) with pull tube (370) and articulation connector (300).

As mentioned above, second lead screw assembly (250) may be substantially similar to first lead screw assembly (230), with the difference of threading (252) having an opposite orientation/threading as compared to threading (232). Therefore, as best seen in FIG. 23C, second lead screw assembly (250) includes a first half (254) and a second half (256) that are substantially similar to first half (232) and second half (236) described above, respectively. First half (254) includes a pair of laterally spaced projections (258), a central projection (260), and a pair of coupling posts (262) substantially similar to laterally spaced projections (238), central projection (240), and couplings posts (242) described above, respectively. Additionally, first half (254) defines an open slot (264), a portion of cavity (268) and a pin hole (255), substantially similar to open slot (244), cavity (248), and pin hole (235) described above, respectively. Second half (256) includes laterally spaced projections (259) and a central projection (261), substantially similar to laterally spaced projections (239) and central projection (241) described above. Additionally, second half (256) defines a pair a coupling holes (263), an open slot (265), cavity (268), and pin hole (255) substantially similar to coupling holes (243), open slots (245), cavity (248), and pin hole (235) described above, respectively.

Figure 20:
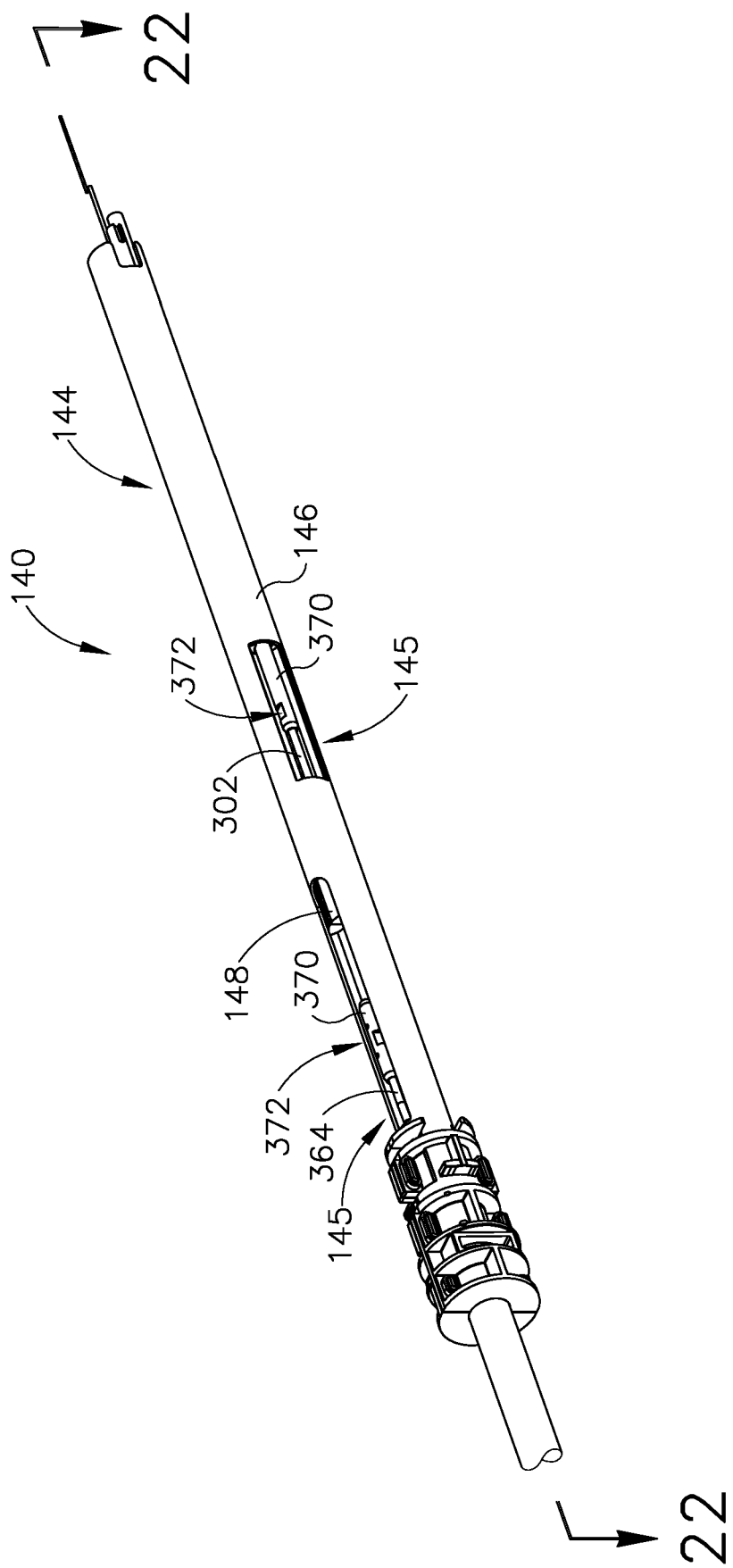
FIG. 20 depicts a perspective view of the proximal portion of the shaft assembly of FIG. 4.
Figure 21:
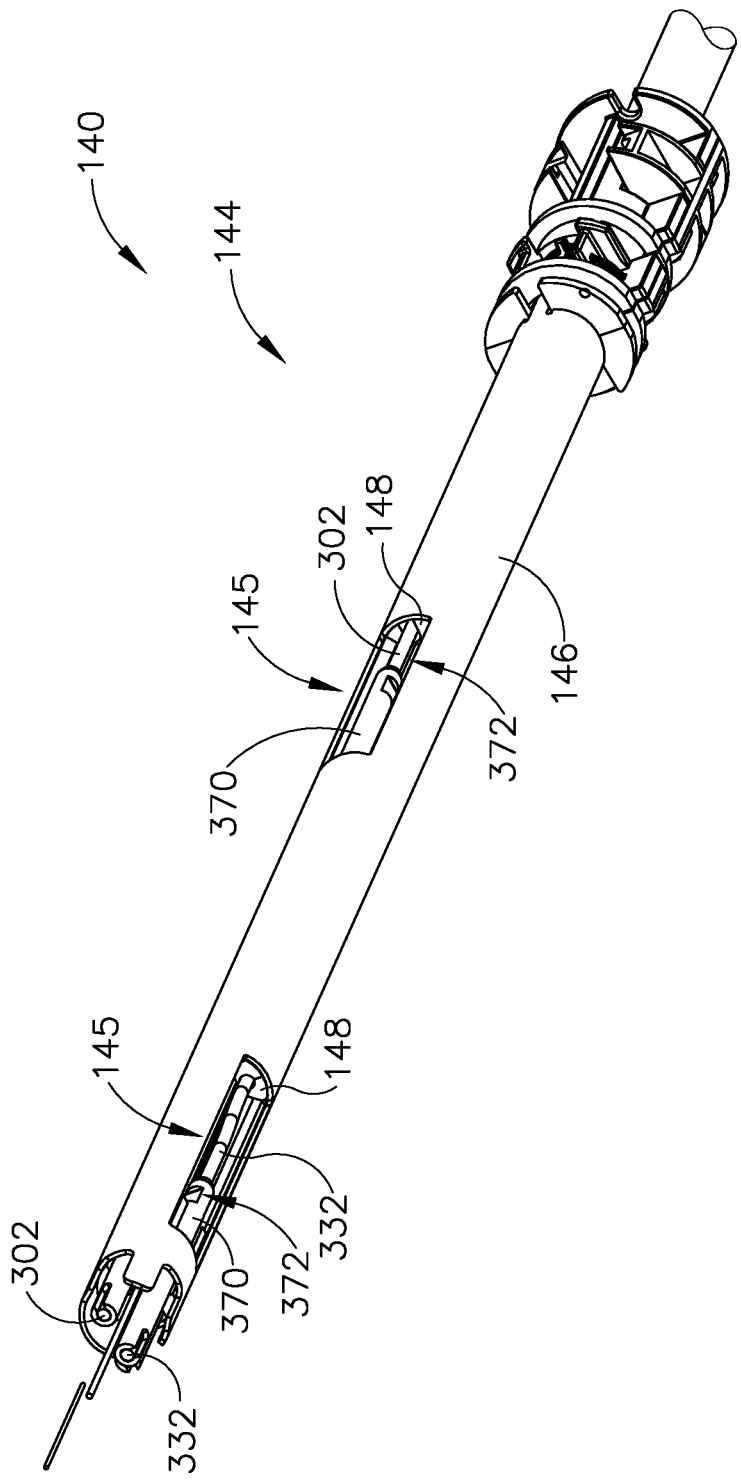
FIG. 21 depicts another perspective view of the proximal portion of the shaft assembly of FIG. 4.
Figure 22:
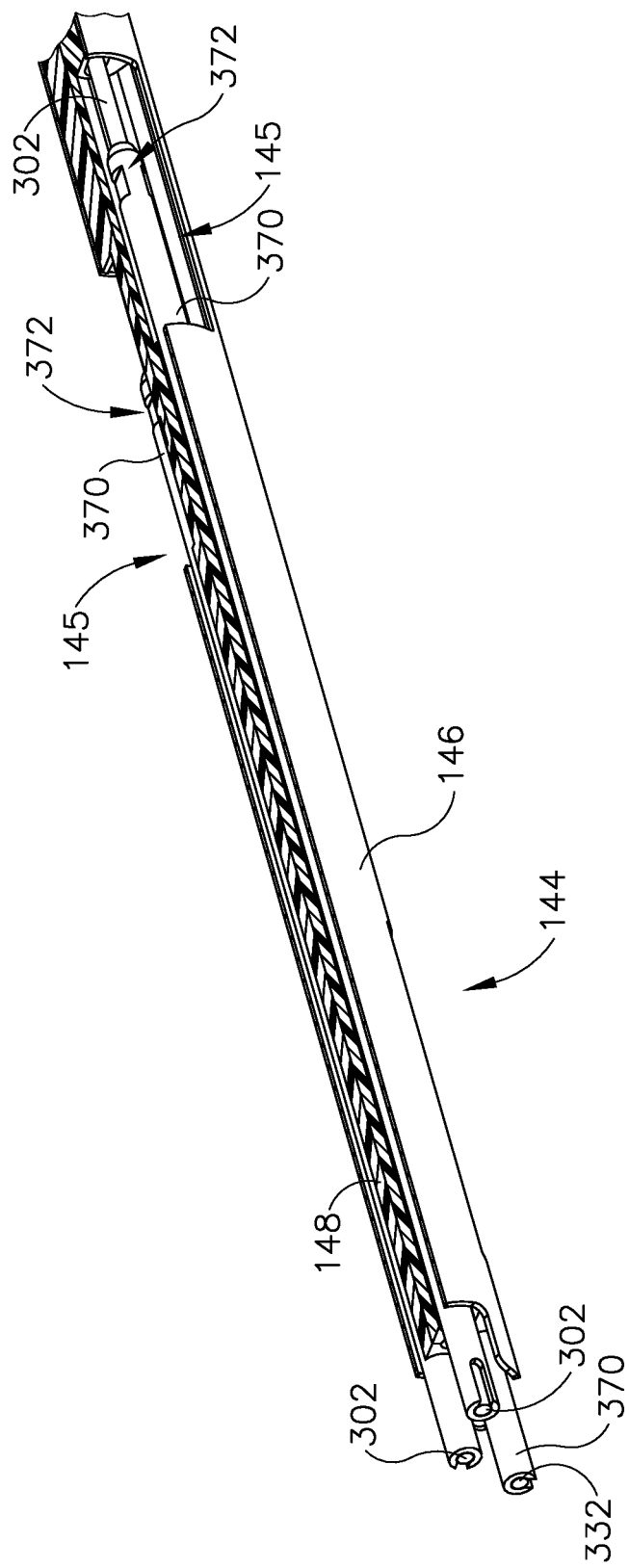
FIG. 22 depicts a cross-sectional perspective view of the proximal portion of the shaft assembly of FIG. 4, taken along line 22-22 of FIG. 20.

FIGS. 20-22 show proximal portion (144) of shaft assembly (140) prior to coupling with yoke (158), articulation drive assembly (200), and knife coupling body (174). As can be seen in FIGS. 20-21, portions of external sheath (146) and housing member (148) associated with proximal portion (144) of shaft assembly (140) define slots (145) at locations where yoke (158), lead screw assemblies (230, 250), and knife coupling body (174) couple with rod portions (332, 302, 364) of jaw closure connector (300), articulation connector (330), and knife member (360), respectively. As mentioned above, rod portions (332, 302, 364) are configured to translate relative to housing member (148) and external sheath (146).

Proximal ends of each rod portion (332, 302, 364) may be attached to a respective pull tube (370). Pull tubes (370) may slide over rod portions (332, 302, 364) and later be fixedly coupled with rod portions (332, 302, 364). Pull tubes (370) may be fixedly coupled with rod portions (332, 302, 364) through any suitable means that would be apparent to one having ordinary skill in the art in view of the teachings herein. For instance, pull tubes (370) and rod portions (332, 302, 364) may be welded together, attached through adhesives, etc. Pull tubes (370) each define a notch (372). Notch (372) is dimensioned to couple with coupling arms (284) such that coupling members (280) are fixed to pull tubes (370) when lead screw assemblies (230, 250) properly house coupling members (280) within respective cavities (248, 268).

Figure 23B:
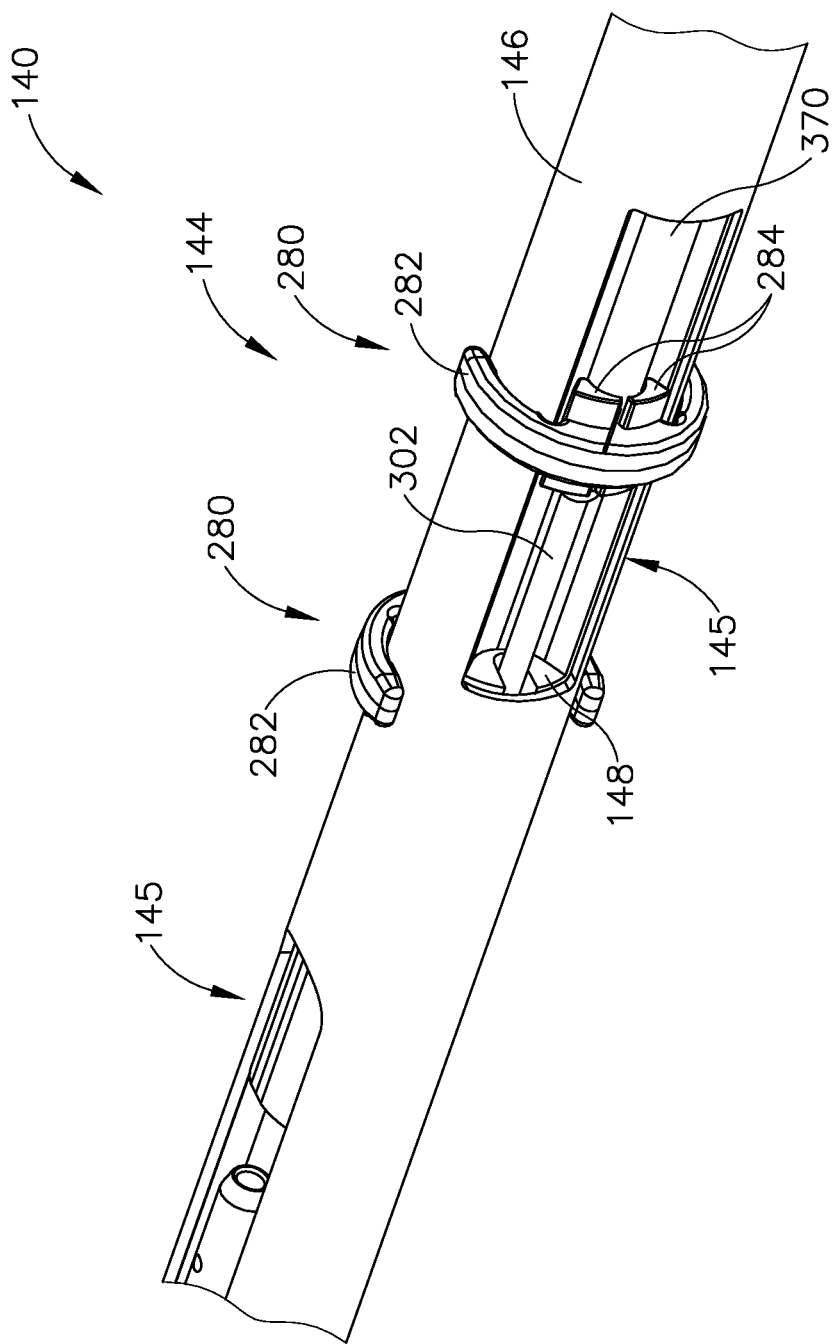
FIG. 23B depicts a perspective view of the pair of coupling members of FIG. 23A attached to respective articulation connectors of FIG. 23A.
Figure 23C:
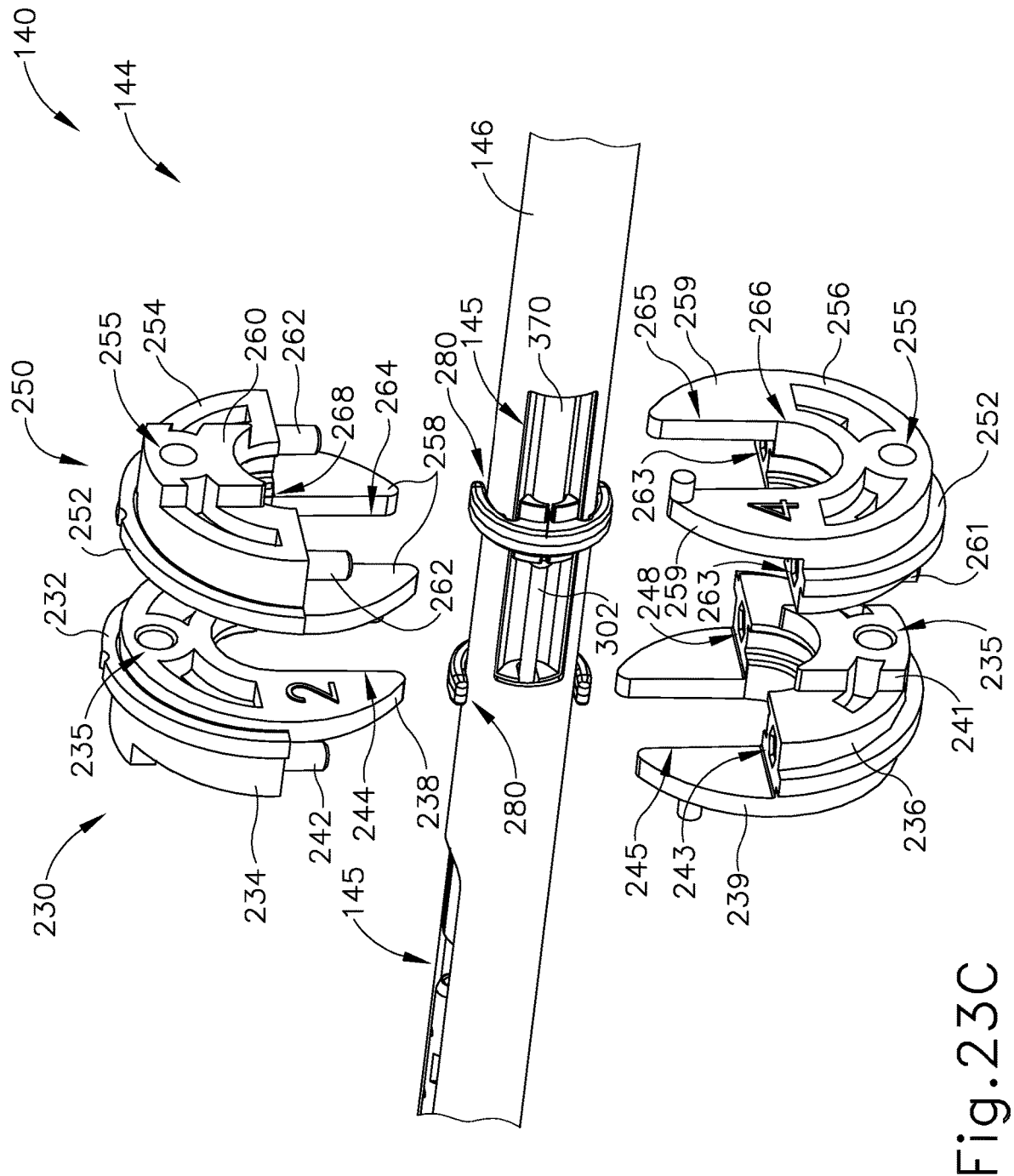
FIG. 23C depicts a pair of lead screw assemblies of FIG. 15 aligned to be attached to respective coupling members of FIG. 23A and the shaft assembly of FIG. 4.

FIGS. 23A-23D show an exemplary assembly of coupling members (280), lead screw assemblies (230, 250), pull tubes (370), and articulation connectors (300) with proximal portion (144) of shaft assembly (140). First, as shown in FIG. 23A, pull tubes (370) are previously inserted over articulation connectors (300). Both pull tubes (370) and articulation connectors (300) are inserted within proximal portion (144) of shaft assembly (140). Next, coupling members (280) are aligned with respective pull tubes (370) such that coupling arms (284) face toward notches (372) of pull tube (370). At this point, pull tube (370) may or may not be fixedly attached with rod portion (302) of articulation connector (300). With coupling arms (284) of coupling members (380) aligned adjacent to notches (372) of pull tubes (370), an operator may then attach coupling members (280) with pull tube (370) via coupling arms (284) and notches (372). Coupling arms (284) may mate with notch (372) such that translation and rotation of coupling arms (284) drives translation and rotation of pull tube (370). In other words, coupling arms (284) may abut against walls of pull tube (370) defining notch (372) to translate and rotate pull tube (370). Coupling arms (284) may couple with notches (372) through any suitable means as would be apparent to one having ordinary skill in the art in view of the teachings herein. For example, coupling arms (284) may snap fit with notches (372), may be attached to notches (372) via adhesives, may rest within notches (372) while lead screw assemblies (230, 250) maintain the position of coupling arms (284) relative to notches (372), etc.

Figure 23D:
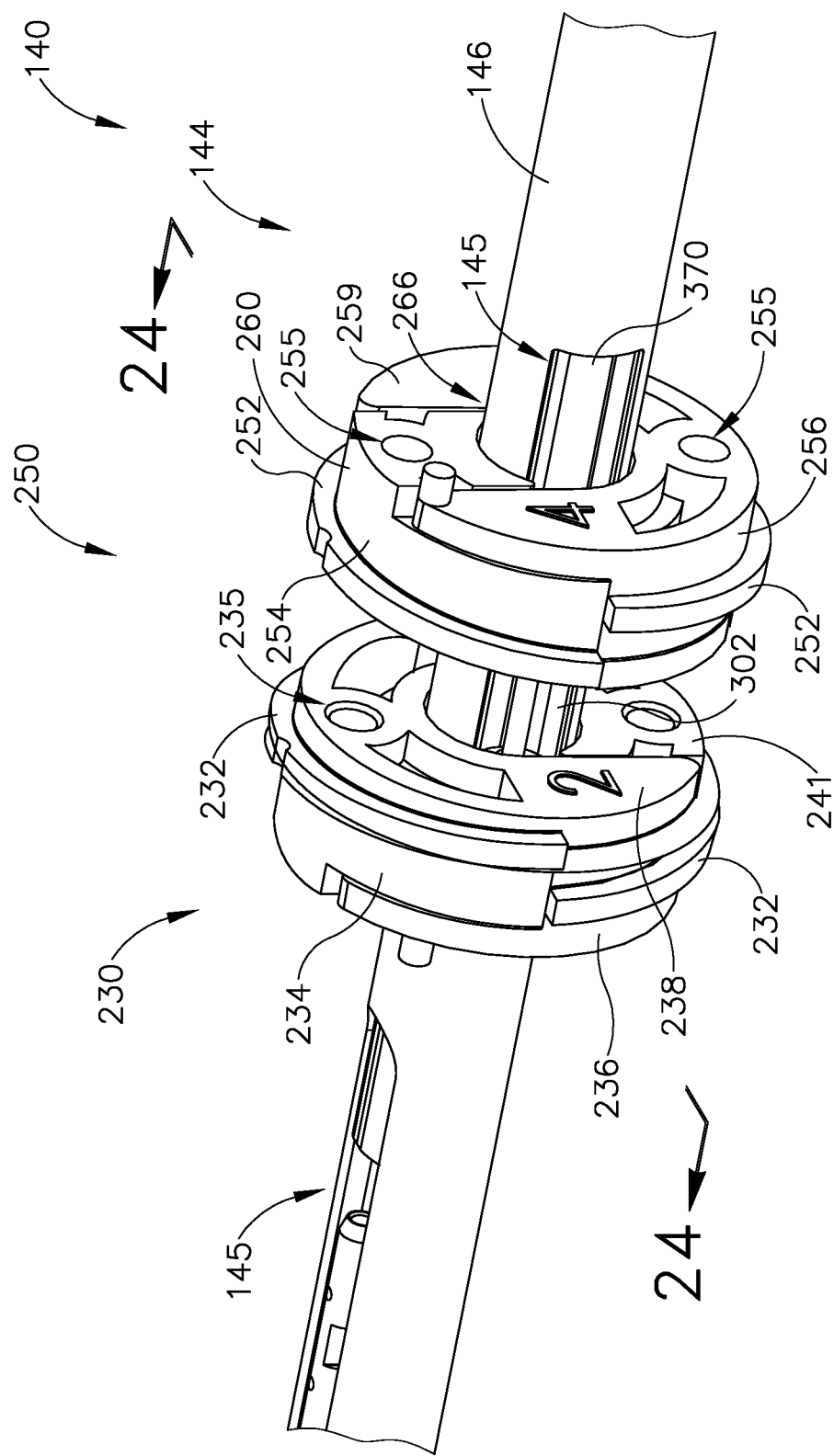
FIG. 23D depicts a pair of lead screw assemblies of FIG. 15 attached to respective coupling members of FIG. 23A and the shaft assembly of FIG. 4.
Figure 24:
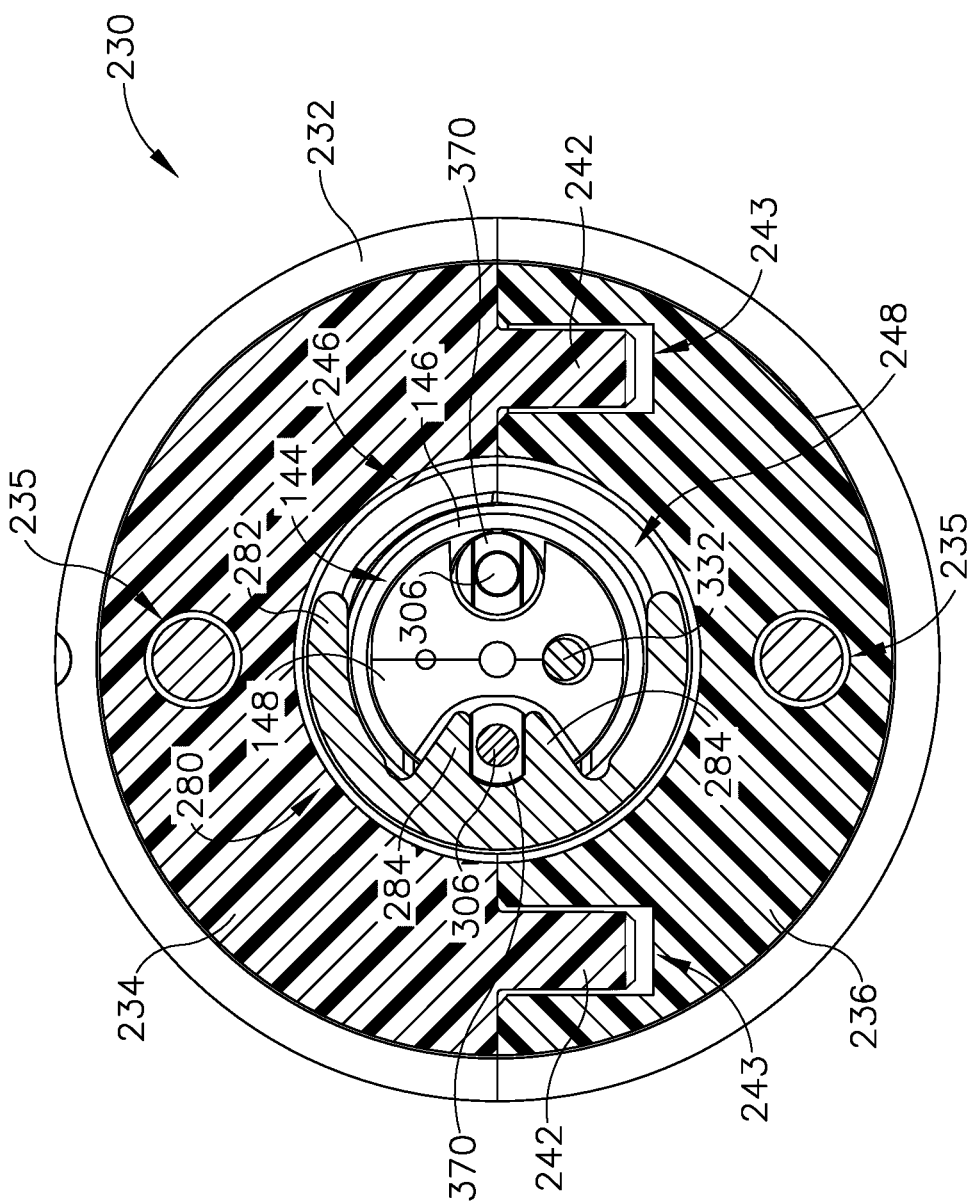
FIG. 24 depicts a rear cross-sectional view of the lead screw assembly of FIG. 15 and the coupling member of FIG. 23A attached to the shaft assembly of FIG. 4.

With coupling members (284) properly attached with pull tubes (370), an operator may then place first halves (234, 254) and second halves (236, 256) of lead screws (230, 250) to a position laterally spaced from external sheath (146) and directly adjacent to their respective coupling members (280). In particular, an operator may place first halves (234, 254) and second halves (236, 256) to a position where cavity (248, 268) defined by first halves (234, 254) and second halves (236, 256) align with arched body (282) of coupling member (280). Next, as shown in FIG. 23D, coupling posts (242, 262) of first halves (234, 254) may then be inserted into post holes (243, 263) of second halves (236, 256) such that first halves (234, 254) and second halves (236, 256) are properly coupled. With first halves (234, 254) and second halves (236, 256) attached, coupling members (280) are now rotatably disposed within cavities (248, 268) of respective lead screw assemblies (230, 250). Additionally, central projections (240, 241, 260, 261) are also housed within respective slots (245, 244, 265, 264); and threading (232, 252) defined by each half (234, 236, 254, 256) are aligned, respectively. At this point, articulation connectors (300) are now coupled with lead screws (230, 250) such that articulation connectors (300) may translate with lead screws (230, 250) relative to shaft assembly (140); and such that articulation connectors (300) may rotate with shaft assembly (140) relative to respective lead screws (230, 250).

Because lead screw assemblies (230, 250) may be assembled from multiple pieces, lead screw assemblies (230, 250) may be laterally attached to external sheath (146) directly with coupling members (280) instead of longitudinally sliding over external sheath (146) to then assemble with coupling members (280). This may reduce tolerance stacking involved with longitudinally sliding lead screw assemblies (230, 250) over external sheath (146) to couple lead screw assemblies (230, 250) with articulation connectors (300).

An operator may now fix pull tubes (370) with articulation connectors (300), if not already done so. Additionally, an operator may now attach rotatable housing (220), proximal cap (210), and distal cap (202) by any suitable means as would be apparent to one having ordinary skill in the art in view of the teachings herein. For instance, an operator may place shaft assembly (140) and lead screws (230, 250) on a fixture to weld pull tubes (370) with articulation connectors (300); and assemble rotatable housing (220), proximal cap (210), and distal cap (202). Proximal cap and distal cap (202) may be attached to shaft assembly (140) at any suitable time within the assembly process describe above as would be apparent to one having ordinary skill in the art in view of the teachings herein.

III. EXEMPLARY COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly defines a longitudinal axis; (c) an articulation section attached to a distal end of the shaft assembly; (d) an end effector located distally relative to the shaft assembly, wherein the end effector is connected to the articulation section such that the end effector is configured to deflect relative to the longitudinal axis defined by the shaft assembly; (e) an articulation connector slidably disposed within the shaft assembly, wherein the articulation connector is configured to translate relative to the shaft assembly to deflect the end effector relative to the longitudinal axis; and (f) an articulation drive assembly, wherein the articulation drive assembly is configured to translate the articulation connector relative to the shaft assembly, wherein the articulation drive assembly comprises: (i) a rotatable housing configured to rotate relative to the body, and (ii) a first lead screw assembly comprising a first half and a second half, wherein the first half is configured to couple with the second half such that the first lead screw assembly is slidably coupled with the shaft assembly.

Example 2

The apparatus of Example 1, wherein first half of the first lead screw assembly comprises a pair of posts, wherein the second half of the first lead screw assembly comprises a pair of post holes configured to receive the pair of posts.

Example 3

The apparatus of Example 2, wherein the pair of posts and the pair of post holes are configured to couple the first half of the first lead screw assembly and the second half of the first lead screw assembly.

Example 4

The apparatus of any one or more of Examples 1 through 3, wherein the end effector comprises at least one electrode operable to apply RF electrosurgical energy to tissue.

Example 5

The apparatus of any one or more of Examples 1 through 4, further comprising a connecting member configured to couple the articulation connector with the first lead screw assembly.

Example 6

The apparatus of Example 5, wherein the first half of the first lead screw assembly and the second half of the first lead screw assembly together define a cavity when coupled, wherein the cavity houses the connecting member.

Example 7

The apparatus of Example 6, wherein the connecting member is rotatably disposed within the cavity.

Example 8

The apparatus of Example 7, wherein the connecting member is longitudinally fixed relative to the first lead screw assembly.

Example 9

The apparatus of any one or more of Examples 6 through 8, wherein the connecting member comprises a pair of coupling arms configured to fix the connecting member with the articulation connector.

Example 10

The apparatus of Example 9, wherein the articulation connector includes a pull tube defining a notch, wherein the coupling arms are configured to interface with the notch defined by the pull tube to fix the connecting member with the articulation connector.

Example 11

The apparatus of Example 10, wherein the connecting member further includes an arched body fixed to the connecting arms, wherein the arched body is housed within the cavity.

Example 12

The apparatus of any one or more of Examples 10 through 11, wherein the connecting arms are resilient.

Example 13

The apparatus of any one or more of Examples 1 through 12, wherein the rotatable housing defines an internal threading, wherein the first half and the second half comprise an external threading configured to mesh with the internal threading of the rotatable member.

Example 14

The apparatus of Example 13, wherein the rotatable housing is configured longitudinally drive the first lead screw assembly along the shaft assembly via camming between the external threading and the internal threading.

Example 15

The apparatus of any one or more of Examples 1 through 14, wherein the first half of the first lead screw assembly further comprises a pair of laterally spaced projections defining an open slot, wherein the second half of the first lead screw assembly further comprises a central projection, wherein the central projection is housed within the open slot when the first half and the second half are coupled.

Example 16

The apparatus of Example 15, wherein the open slot further defines a shaft through hole configure to slidably house a portion of the shaft assembly.

Example 17

The apparatus of Example 16, wherein the second half of the first lead screw assembly is configured to cooperate with the first half of the first lead screw assembly to define the shaft through hole.

Example 18

The apparatus of any one or more of Examples 1 through 17, further comprising a second lead screw assembly coupled with a second articulation connector, where the second articulation connector is slidably disposed within the shaft assembly.

Example 19

An apparatus comprising: (a) a body; (b) a shaft assembly extending distally from the body, wherein the shaft assembly defines a longitudinal axis; (c) an articulation section attached to a distal end of the shaft assembly; (d) an end effector located distally relative to the shaft assembly, wherein the end effector is connected to the articulation section such that the end effector is configured to deflect relative to the longitudinal axis defined by the shaft assembly; (e) an articulation connector slidably disposed within the shaft assembly, wherein the articulation connector is configured to translate relative to the shaft assembly to deflect the end effector relative to the longitudinal axis; and (f) an articulation drive assembly, wherein the drive assembly is configured to translate the articulation connector relative to the shaft assembly, wherein the articulation drive assembly comprises: (i) a rotatable housing configured to rotate relative to the body, wherein the rotatable housing defines a first internal threading and a second internal threading, (ii) a first lead screw assembly comprising a first half and a second half, wherein the first half and the second half are configured to couple with each other to slidably receive the shaft assembly, wherein the first lead screw assembly is configured to mesh with the first internal threading when the first half and the second half are coupled, and (iii) a second lead screw assembly comprising a third half and a fourth half, wherein the third half and the fourth half are configured to couple with each other to slidably receive the shaft assembly, wherein the second lead screw assembly is configured to mesh with the second internal threading when the third half and the fourth half are coupled.

Example 20

An apparatus comprising: (a) a body; (b) a shaft assembly extending distally from the body, wherein the shaft assembly defines a longitudinal axis; (c) an articulation section attached to a distal end of the shaft assembly; (d) an end effector located distally relative to the shaft assembly, wherein the end effector is connected to the articulation section such that the end effector is configured to deflect relative to the longitudinal axis defined by the shaft assembly; (e) an articulation connector slidably disposed within the shaft assembly, wherein the articulation connector is configured to translate relative to the shaft assembly to deflect the end effector relative to the longitudinal axis; and (f) an articulation drive assembly, wherein the drive assembly is configured to translate the articulation connector relative to the shaft assembly, wherein the articulation drive assembly comprises: (i) a rotatable housing configured to rotate relative to the body, (ii) a first lead screw assembly comprising a first half and a second half, wherein the first half is configured to couple with the second half such that the first lead screw assembly is slidably coupled with the shaft assembly, wherein the first half and the second half are configured to define a cavity when coupled together, and (iii) a coupling member housed within the cavity of the first lead screw assembly, wherein the coupling member is fixed to the articulation connector.

IV. MISCELLANEOUS

It should be understood that any of the versions of the instruments described herein may include various other features in addition to or in lieu of those described above. By way of example only, any of the devices herein may also include one or more of the various features disclosed in any of the various references that are incorporated by reference herein. For instance, the teachings herein may be readily combined with various teachings in U.S. Pat. No. 9,526,565, the disclosure of which is incorporated by reference herein; U.S. Pat. No. 9,492,224, the disclosure of which is incorporated by reference herein; and/or U.S. Pub. No. 2016/0100882, issued as U.S. Pat. No. 10,292,758 on May 21, 2019, the disclosure of which is incorporated by reference herein. Various suitable ways in which such teachings may be combined will be apparent to those of ordinary skill in the art.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a shaft assembly defining a longitudinal axis;

(b) an articulation section;
(c) an end effector located distally relative to the shaft assembly, wherein the articulation section is configured to deflect the end effector relative to the longitudinal axis;
(d) an articulation connector disposed within the shaft assembly, wherein the articulation connector is configured to actuate relative to the shaft assembly to drive deflection of the end effector relative to the longitudinal axis, wherein the articulation connector comprises a pull tube and a rod portion extending distally from the pull tube; and
(e) an articulation drive assembly configured to actuate the articulation connector relative to the shaft assembly, wherein the articulation drive assembly comprises:
(i) an input assembly, and
(ii) a first output assembly driven by the input assembly, wherein the first output assembly is coupled with the articulation connector such that the first output assembly is configured to drive actuation of the articulation connector relative to the shaft assembly via the input assembly, wherein the first output assembly comprises:
(A) a first body defining an opening, and
(B) a second body comprising a complementary projection, wherein the second body is configured to couple with the first body via the complementary projection and the opening such that the first body and the second body are operatively coupled with the articulation connector.

2. The apparatus of claim 1, wherein the input assembly comprises a rotatable housing.

3. The apparatus of claim 2, wherein the rotatable housing defines a first threaded region.

4. The apparatus of claim 3, wherein the first body comprises a first threaded member, wherein the second body comprises a second threaded member, wherein the first threaded member and the second threaded member are configured to operatively engage the first threaded region of the rotatable housing.

5. The apparatus of claim 1, wherein the complementary projection of the second body further comprises a coupling post.

6. The apparatus of claim 1, wherein the pull tube and the rod portion are rotationally coupled with the first output assembly.

7. The apparatus of claim 6, wherein the articulation connector further comprises a connecting body attached to the pull tube and rotationally disposed within the first output assembly.

8. The apparatus of claim 7, wherein the connecting body comprises a pair of arms, wherein the pull tube comprises a pair of flats, wherein the connecting body and the pull tube are fixed to each other via the pair of arms and the pair of flats.

9. The apparatus of claim 1, further comprising a second articulation connector, wherein the input assembly is configured to simultaneously actuate the articulation connector and the second articulation connector in opposing directions.

10. The apparatus of claim 9, wherein the articulation drive further comprises a second output assembly driven by the input assembly, wherein the second output assembly is coupled with the second articulation connector such that the second output assembly is configured to drive actuation of the second articulation connector relative to the shaft assembly via the input assembly.

11. The apparatus of claim 10, wherein the second output assembly comprises a third body and a fourth body, wherein the fourth body is configured to couple with the third body such that the third body and the fourth body are operatively coupled with the second articulation connector.

12. The apparatus of claim 11, wherein the third body and the fourth body are configured to couple with each other via a second opening and a second complementary projection.

13. The apparatus of claim 1, wherein further comprising a handle assembly, wherein the shaft assembly extends distally from the handle assembly.

14. The apparatus of claim 13, wherein the articulation drive assembly is housed within the handle assembly.

15. An apparatus, comprising:
(a) a shaft assembly defining a longitudinal axis;
(b) an end effector;
(c) an articulation section configured to deflect the end effector relative to the longitudinal axis; and
(d) an articulation drive assembly, comprising:
(i) an elongated drive member disposed within the shaft assembly, wherein the elongated drive member is configured to translate relative to the shaft assembly to drive deflection of the end effector relative to the longitudinal axis, and
(ii) a connector coupling slidably coupled with the shaft assembly, wherein the shaft assembly and the elongated drive member are configured to rotate about the longitudinal axis relative to the connector coupling, wherein the connector coupling is configured to drive translation of the elongated drive member relative to the shaft assembly, wherein the connector coupling comprises:
(A) a first body comprising a first coupling feature, wherein the first body defines a first semi-annular recessed channel, and
(B) a second body comprising a complementary coupling feature configured to engage the first coupling feature to couple the second body with the first body such that the first body and the second body are fixed relative to each other, wherein the second body defines a second semi-annular recessed channel, and
(iii) a coupling body comprising a pair of protrusions configured to selectively affix the coupling body to the elongated drive member,
wherein the first semi-annular recessed channel and the second semi-annular recessed channel together form a continuous annular recessed channel dimensioned to rotationally house the coupling body while the first body and the second body are coupled to each other such that the pair of protrusions radially inwardly from the continuous annular recessed channel,
wherein the first body and the second body, while coupled with each other, are configured to operatively couple with the elongated drive member.

16. The apparatus of claim 15, wherein the end effector comprises a first jaw and a second jaw pivotally coupled with the first jaw.

17. The apparatus of claim 16, wherein the end effector further comprises a first electrode surface and a second electrode surface.

18. The apparatus of claim 15, wherein the elongated drive member is rotatable relative to the connector coupling.

19. An apparatus, comprising:
(a) a shaft assembly defining a longitudinal axis;
(b) an end effector;

(c) an articulation section configured to deflect the end effector relative to the longitudinal axis; and
(d) an articulation drive assembly, comprising:
  (i) an elongated drive member disposed within the shaft assembly, wherein the elongated drive member is configured to translate relative to the shaft assembly to drive deflection of the end effector relative to the longitudinal axis, and
  (ii) a connector coupling slidably coupled with shaft assembly, wherein the connector coupling is coupled with the elongated drive member such that actuation of the connector coupling relative to the shaft assembly is configured to drive actuation of the elongated drive member relative to the shaft assembly, wherein the connector coupling comprises:
    (A) a first half, and
    (B) a second half configured to couple with the first half in order to slidably receive the shaft assembly, wherein the first half and the second half are fixed relative to each other while coupled, and
  (iii) a connecting member comprising a pair of protrusions, wherein the connecting member is rotationally disposed within an arched cavity defined by the first half and the second half such that the pair of protrusions extend radially inwardly from the arched cavity, wherein the connecting member is configured to, prior to being rotationally disposed with the arched cavity, selectively couple with the elongated drive member such that the connecting member is fixed to the elongated drive member.

* * * * *